United States Patent
Ray et al.

(10) Patent No.: US 9,996,963 B2
(45) Date of Patent: Jun. 12, 2018

(54) DEVICES, FRAMEWORKS AND METHODOLOGIES FOR ENABLING USER-DRIVEN DETERMINATION OF BODY SIZE AND SHAPE INFORMATION AND UTILISATION OF SUCH INFORMATION ACROSS A NETWORKED ENVIRONMENT

(71) Applicant: MPORT PTY LTD, Artarmon (AU)

(72) Inventors: Dipra Ray, Macquarie Park (AU); Melody Shiue, Macquarie Park (AU); Tsung Yuan Wu, Macquarie Park (AU); John Quinn, Macquarie Park (AU)

(73) Assignee: MPORT PTY LTD, Macquarie Park (AU)

(*) Notice: Subject to any disclaimer, the term of this patent is extended or adjusted under 35 U.S.C. 154(b) by 0 days. days.

(21) Appl. No.: 14/890,541

(22) PCT Filed: May 13, 2014

(86) PCT No.: PCT/AU2014/000514
§ 371 (c)(1),
(2) Date: Nov. 11, 2015

(87) PCT Pub. No.: WO2014/183157
PCT Pub. Date: Nov. 20, 2014

(65) Prior Publication Data
US 2016/0093085 A1 Mar. 31, 2016

(30) Foreign Application Priority Data
May 13, 2013 (AU) ................. 2013901684
May 13, 2013 (AU) ................. 2013901685

(51) Int. Cl.
*G06T 13/40* (2011.01)
*G06T 19/20* (2011.01)
(Continued)

(52) U.S. Cl.
CPC ............ *G06T 13/40* (2013.01); *A61B 5/0022* (2013.01); *A61B 5/1072* (2013.01);
(Continued)

(58) Field of Classification Search
CPC ...................................................... G06T 13/40
See application file for complete search history.

(56) References Cited

U.S. PATENT DOCUMENTS

| 7,184,047 B1 | 2/2007 | Crampton |
| 2005/0101884 A1 | 5/2005 | Weeks et al. |

(Continued)

FOREIGN PATENT DOCUMENTS

| WO | 2007096652 A2 | 8/2007 |
| WO | 2014183157 A1 | 11/2014 |

OTHER PUBLICATIONS

Supplementary European Search Report, European Application No. 14798065.0, dated Sep. 16, 2016, 7 pages.
(Continued)

*Primary Examiner* — Daniel Hajnik
(74) *Attorney, Agent, or Firm* — Nelson Mullins Riley & Scarborough LLP

(57) ABSTRACT

A scanning booth with a user interface. The interface receives user identification or registration data and provides instructional prompts for the user to assume various predefined positions, stances and postures. Image data of each pose is captured using scanning devices in the booth. A three dimensional avatar is generated based on the mapping or morphing of image data to a generic avatar model. Data from the generated model is transmitted to a server where it is stored in a database for later account application in, for example, garment sizing, display or fitting, or health monitoring.

16 Claims, 27 Drawing Sheets

(51) Int. Cl.
  *A61B 5/00*    (2006.01)
  *A61B 5/107*   (2006.01)
  *G06F 19/00*   (2018.01)
  *G06T 3/40*    (2006.01)
  *G06T 5/00*    (2006.01)
  *G06T 7/60*    (2017.01)
  *H04N 5/33*    (2006.01)
  *A63B 24/00*   (2006.01)

(52) U.S. Cl.
  CPC ............ *A61B 5/6888* (2013.01); *A61B 5/744* (2013.01); *A61B 5/7435* (2013.01); *G06F 19/3437* (2013.01); *G06F 19/3481* (2013.01); *G06T 3/40* (2013.01); *G06T 5/002* (2013.01); *G06T 7/60* (2013.01); *G06T 19/20* (2013.01); *H04N 5/33* (2013.01); *A61B 5/4561* (2013.01); *A61H 2230/85* (2013.01); *A63B 2024/0096* (2013.01); *A63B 2230/62* (2013.01); *G06T 2200/04* (2013.01); *G06T 2200/08* (2013.01); *G06T 2200/12* (2013.01); *G06T 2200/24* (2013.01); *G06T 2207/10004* (2013.01); *G06T 2207/10048* (2013.01); *G06T 2207/30196* (2013.01); *G06T 2210/16* (2013.01); *G06T 2210/41* (2013.01); *G06T 2210/44* (2013.01); *G06T 2215/16* (2013.01); *G06T 2219/2016* (2013.01); *G06T 2219/2021* (2013.01)

(56) References Cited

U.S. PATENT DOCUMENTS

| | | | | |
|---|---|---|---|---|
| 2005/0113650 | A1* | 5/2005 | Pacione | A61B 5/411 600/300 |
| 2009/0281420 | A1* | 11/2009 | Passmore | G06T 7/0016 600/425 |
| 2010/0157021 | A1 | 6/2010 | Abraham et al. | |
| 2011/0025689 | A1* | 2/2011 | Perez | A63F 13/63 345/420 |
| 2012/0086783 | A1* | 4/2012 | Sareen | G06N 3/006 348/47 |
| 2012/0120257 | A1* | 5/2012 | Corn | H04N 1/00132 348/207.1 |
| 2013/0296711 | A1* | 11/2013 | Curiel | A61B 5/0077 600/476 |
| 2014/0176565 | A1* | 6/2014 | Adeyoola | G06T 19/006 345/473 |

OTHER PUBLICATIONS

International Search Report, PCT/AU2014/000514, dated Aug. 25, 2014, 7 pages.
Extended European Search Report, European Application No. 14798065.0, dated Jan. 12, 2017, 12 pages.

\* cited by examiner

```
OPTION UNITS=cm
#DATE=2013, 03, 23
MEASURE FrontNeckBaseHeight=140.6
MEASURE BackNeckHeight=146.6
MEASURE BustHeight=124.6
MEASURE ChestHeight=129.1
MEASURE UnderbustHeight=120.1
MEASURE WaistHeight=96.6
MEASURE HipHeight=84.6
MEASURE TopHipHeight=90.6
MEASURE UpperHipHeight=93.6
MEASURE BustGirth=107.1
MEASURE BustArcWidth=53.9
MEASURE UnderBustGirth=102.2
```

Figure 12D

```
<Hip Hip="0.989936" Morph="HIPS_LARGE_WHOLE" Value="0.5">
</Hip>
<Hip Hip="0.996738" Morph="HIPS_LARGE_WHOLE" Value="0.6">
</Hip>
<Hip Hip="1.003658" Morph="HIPS_LARGE_WHOLE" Value="0.7">
</Hip>
```

```
MEASURE FrontUpperHipGirth=43.7
MEASURE TopHipGirth=95.5
MEASURE FrontTopHipGirth=44.1
MEASURE HipGirth=99.8
MEASURE FrontHipGirth=46.8
MEASURE ChestGirth=113.1
```

Figure 12E

DEVICES, FRAMEWORKS AND METHODOLOGIES FOR ENABLING USER-DRIVEN DETERMINATION OF BODY SIZE AND SHAPE INFORMATION AND UTILISATION OF SUCH INFORMATION ACROSS A NETWORKED ENVIRONMENT This application is a 35 U.S.C. 371 national stage filing of International Application No. PCT/AU2014/000514, filed on May 13, 2014. The contents of the aforementioned applications are hereby incorporated by reference in their entireties.

FIELD OF THE INVENTION

The present invention relates to devices, frameworks and methodologies for enabling user-driven determination of body shape information and utilisation of such information across a networked environment. For example, some embodiments relate to devices (comprising both hardware and software elements) which enable a user to autonomously operate body scanning hardware without further human assistance, thereby to provide to a computer system body shape information. Some embodiments relate to technology by which such body shape information is utilised, for example in providing sizing information to third party websites. Whilst the disclosure herein is focussed on a selection of such embodiments, it will be appreciated that the invention finds application in further contexts.

BACKGROUND

Any discussion of the prior art throughout the specification should in no way be considered as an admission that such prior art is widely known or forms part of common general knowledge in the field.

Body size and shape information is highly useful in a range of situations, including selection and sizing of clothing, and monitoring of health and/or fitness. Various known hardware devices enable determination of such information, resulting in the generation of digital data which represents. However, in spite of hardware availability, there are significant challenges in providing solutions which enable widespread consumer utilisation of such data in a convenient manner.

SUMMARY OF THE INVENTION

One embodiment provides a scanning booth system configured to enable determination of physical body shape data for a user, the system including:

a structural assembly defining a booth interior, wherein the booth interior is securely concealed from exterior view, and wherein the booth interior is sized thereby to enable undressing and dressing of a user contained therein;

a user interface device configured to receive identification information from a user;

one or more stimuli devices coupled to a control device, wherein the control device is configured to implement a logical instructions process flow thereby to provide, via the one or more stimuli devices, instructions to a user contained within the booth interior, wherein the instructions include instructions for the user to adopt a predefined stance, position and posture;

one or more scanning devices configured to derive measurements representative of size of a body contained within the booth interior;

a communications module configured to enable communication between the scanning booth and a central server, wherein the communications module is configured to transmit, to the central server, body scan data derived from output of the one or more scanning devices; and a display unit configured to provide to the user a visual representation of a three dimensional avatar defined based upon the output of the one or more scanning devices.

One embodiment provides a system wherein the structural assembly includes handles which are configured to be manually grasped, thereby to provide instructions as to body pose. That is, in use, a user grasps the handles, thereby to adopt an appropriate body position for infrared-based body scanning.

One embodiment provides a system wherein the structural assembly includes a floor including a primary-textured region and a secondary-textured region, such that a user is able to determine when they are standing in the secondary-textured region, thereby to provide instructions as to stance. For example, the secondary-textured region may be defined by a pair of smooth foot-shaped regions in an otherwise carpeted floor.

One embodiment provides a system wherein the user interface device is configured to enable each of the following: input of user identification information representative of a user account previously created at the scanning booth; input of user identification information representative of a user account previously created at a further scanning booth; input of user identification information representative of a user account previously created via a user client terminal that interacts with a web server; and generation of a new user account.

One embodiment provides a system wherein the scanning devices include a plurality of scanning cameras in the form of infrared scanners.

One embodiment provides a system 1 wherein the three-dimensional avatar is generated by morphing a generic base avatar based on comparison with measurements devices from operation of the one or more scanning devices, thereby to define an avatar having size parameters representative of the user.

One embodiment provides a system wherein the three-dimensional avatar is generated by applying a shrink-wrapping and smoothing algorithm to point cloud data obtained from infrared scan data thereby to provide an indicative representation of the user based on the user's size parameters.

One embodiment provides a system wherein the three dimensional avatar is not a direct graphical representation of the user.

One embodiment provides a system wherein the three dimensional avatar is uploaded to the server, and made available for embedding into user interface objects in third party websites.

One embodiment provides a system wherein the three dimensional avatar is configured to provide a graphical indication size of a specified garment relative to size of the user One embodiment provides a scanning booth system configured to enable determination of physical body shape data for a user, the system being configured to enable user-driven autonomous collection of body scan data for upload to a central server that maintains user account data for the user, wherein the scanning booth includes one or more stimuli devices configured to implement a logical process flow which guides the user through a scanning data collection process without a need for assistance by a further human user.

One embodiment provides a data management system including:

an input interface configured to receive, from a plurality of scanning booth systems according to any preceding claim, body scan data respectively defined for a plurality of users;

a data repository configured to maintain user record data, wherein the user record data is configured to include, for each of a plurality of users, user registration data and user body scan data; and one or more integration modules, wherein the integration modules are configured to provide one or more aspects of the body scan data to one or more third party platforms.

One embodiment provides a system wherein the one or more third party platforms include third party web pages.

One embodiment provides a system wherein each third party web page includes embedded code referencing a widget object served by the one or more integration modules.

One embodiment provides a system wherein the one or more third party platforms include third party software applications which interact with the one or more integration modules via an API.

One embodiment provides a system wherein the integration modules include an integration module configured to assist in identifying garments, displayed on a third party website, which are suitable based on a given user's sizing data as derived from body scan data.

According to one example, there is provided herein a system for determining body shape information associated with a physical body of a user, where the system includes: a processing system; and, a scanning system for scanning the physical body, the scanning system being configured to communicate with the processing system to provide scanned information associated with the physical body to the processing system, wherein the processing system receives the scanned information from the scanning system, and determines body shape information associated with the scanned information.

The system can generate a representation of the physical body, where the representation is typically generated based on the body shape information. In one particular example, the representation can be a three-dimensional (3D) avatar of the physical body, and can include a plurality of 3D avatar images provided to the user, via a user interface.

In yet a further embodiment, the representation can be in proportion to the physical body, and thus can have avatar measurements in proportion to the actual physical measurements of the physical body.

In yet another example, the processing system and the scanning system can be provided in a booth, where the user can enter the booth to obtain the representation from the system.

Thus, for example, the booth is at a height taller than the user standing in the booth. The booth can also include a standing area on a floor area of the booth, the standing area being indicative of where the user stands for scanning. In a further embodiment, the standing area can include a weighing machine for weighing the user.

Furthermore, the booth can also include one or more user interface displays, in communication with the processing system, for providing the user with any one or a combination of: scanning instructions; scanning progress; a representation of the physical body; a health report; a goal indication; an exercise report; a progress report; and, a fashion recommendation In yet a further embodiment, the system can determine user posture information, the user posture information being used to determine a representation of the physical body. In another example, the system can determine user weight information, the user weight information being used to determine a representation of the physical body. And in another example, the system can determine user height information, the height information being used to determine a representation of the physical body. According to one particular example, the height information can be determined by an ultrasonic sensor and/or infrared scanning.

In another example, the scanning system can include one or more scanning cameras for scanning the physical body. Thus, in a particular example, the scanned information can include basic body measurements obtained by the one or more scanning cameras. As used herein, the term "cameras" should be read broadly to include a wide range of scanning components, for example various suitable sensors, including infrared (IR) sensors. The term "camera" is by no means limited to conventional optical cameras.

According to yet another form, there is provided herein a method for determining body shape information associated with a physical body of a user, the method including the steps of, in a processing system: receiving scanned information associated with the physical body, the scanned information being received from a scanning system in communication with the processing system; and, determining body shape information associated with the scanned information.

In yet one example, the method can further include generating a representation of the physical body in accordance with the body shape information.

In another example, the method can include generating a three dimensional avatar of the physical body and displaying the avatar to the user on a display. According to a further embodiment, determining body shape information can includes generating one or more measurements associated with key body parts.

According to another example, the method can include generating any one or a combination of vertical measurements; and, horizontal measurements (for example thereby to determine various contours, circumferences, slopes, volumes, cross-sectional areas, and so on). The method can further include determining body shape type in accordance with the one or more measurements.

In one particular example, the method can include: comparing the determined body shape type with pre-determined body shape types; and making sizing recommendation. These sizing recommendations may be garment/brand specific based on sizing information associated with the garment/brand In some cases this may include and/or extend to determining a fashion choice; and, recommending the sizing and/or fashion choice to the user.

In yet a further embodiment, determining the fashion choice can include accessing fashion item information associated with a fashion item, the fashion item information including item measurement information. In yet another example, generating one or more measurements can include generating one or more fit points of the physical body.

According to one further embodiment, the method can include: comparing the one or more fit points with pre-determined fit points associated with a fashion choice; and, if there is a substantial match, recommending the fashion choice.

In another example, the method can include generating one or more health indicators in accordance with the scanned information. The health indicators can include any one or a combination of the user's: body mass index; waist/hip ratio; fat content; waist circumference; waist/height ratio; waist measurement; height measurement; chest measurement; weight measurement; upper waist measurement, left/right bicep measurement, left/right thigh measurement; and, left/right calf measurements. This may additionally include assessment based on rankings and/or demographic analysis.

According to another example, the method further includes: receiving user goal information; receiving updated scanned information; and, tracking user goal information.

In another example, the method can further include generating a health report. The method can further include providing a customised exercise plan.

According to one particular example, the processing system can include a first (or primary) processing system and a second (or secondary) processing system, communicating with each other to perform the steps of the methods/processes described herein.

In one example, the method can include, in the first processing system: submitting a request to the second processing system to perform one or more steps of any one of the processes/methods described herein; and, receiving an indication that the one or more steps has been completed.

The method can further include, in yet another example: comparing scanned data with pre-determined avatar data; and, creating one or more user avatar representations in accordance with the comparison. using scanned data such as key body landmark positions and the set of scanned points comprising the surface of the scanning subject (the point cloud) to create realistic user avatar.

According to a further embodiment, creating one or more user avatar representations can include scaling, positioning and resizing of the anatomically realistic base 3D model to match the data received from the scanner, specifically: the key body landmarks and the set of scanned points that comprise the surface of the body of the scanning subject (the point cloud). The method can include determining a gender specific base avatar; generating a the personalised avatar by scaling, repositioning and resizing until the base avatar represents the body type; and, storing the resulting avatar data in a data store.

One embodiment provides a computer program product for performing a method as described herein.

One embodiment provides a non-transitive carrier medium for carrying computer executable code that, when executed on a processor, causes the processor to perform a method as described herein.

One embodiment provides a system configured for performing a method as described herein.

Reference throughout this specification to "one embodiment", "some embodiments" or "an embodiment" means that a particular feature, structure or characteristic described in connection with the embodiment is included in at least one embodiment of the present invention. Thus, appearances of the phrases "in one embodiment", "in some embodiments" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

As used herein, unless otherwise specified the use of the ordinal adjectives "first", "second", "third", etc., to describe a common object, merely indicate that different instances of like objects are being referred to, and are not intended to imply that the objects so described must be in a given sequence, either temporally, spatially, in ranking, or in any other manner.

In the claims below and the description herein, any one of the terms comprising, comprised of or which comprises is an open term that means including at least the elements/features that follow, but not excluding others. Thus, the term comprising, when used in the claims, should not be interpreted as being limitative to the means or elements or steps listed thereafter. For example, the scope of the expression a device comprising A and B should not be limited to devices consisting only of elements A and B. Any one of the terms including or which includes or that includes as used herein is also an open term that also means including at least the elements/features that follow the term, but not excluding others. Thus, including is synonymous with and means comprising.

As used herein, the term "exemplary" is used in the sense of providing examples, as opposed to indicating quality. That is, an "exemplary embodiment" is an embodiment provided as an example, as opposed to necessarily being an embodiment of It will be appreciated that any of the features of the methods and systems described herein can be provided independently or any combination with each other.

Furthermore, it will be appreciated that the methods and systems described herein can provide numerous advantages, including, but not limited to providing a system and method which can accurately measure a physical body and provide an accurate anatomically realistic representation of the physical body, typically in an image form. The image of the physical body and associated data generated (for example scanned information or measurement data) can be used to provide certain recommendations to the user of the physical body. In one example, these include fashion and/or health recommendations, although it will be appreciated that other applications of the system and method described herein also fall within the scope of this document.

BRIEF DESCRIPTION OF THE DRAWINGS

Embodiments of the technology are further described by way of example with reference to the accompanying drawings.

FIG. 12B to FIG. 12J are schematic representations of example screen shots showing generations of user body representations and avatars as described herein.

FIG. 13A and FIG. 13B are flow diagrams of an example application of the methods and systems described herein.

DETAILED DESCRIPTION

Described herein are devices, frameworks and methodologies for enabling user-driven determination of body shape information and utilisation of such information across a networked environment. For example, some embodiments relate to devices (comprising both hardware and software elements) which enable a user to autonomously operate body scanning hardware without further human assistance, thereby to provide to a computer system body shape information. Some embodiments relate to technology by which such body shape information is utilised, for example in providing sizing information to third party websites. Whilst the disclosure herein is focussed on a selection of such embodiments, it will be appreciated that the invention finds application in further contexts.

General Overview

The technology herein described relates to distributed collection and utilisation of body scan data, primarily body size and shape information. This data is collected via distributed hardware devices, which preferably include autonomous scanning booths. These booths are "autonomous" in the sense that a user is able to operate the booth autonomously without assistance from another local human user. For example, the booth includes user interface components which implement a predefined logical process thereby to guide a user though a scanning procedure. Body scan data is then uploaded to a central server, and via this server is made available to one or more third party platforms, such as websites and software applications (for example using APIs, widgets, and the like). This enables the third party platforms to implement functionalities which leverage body scan data. Examples of such functionalities include selection of appropriately sized clothing, monitoring of health and fitness, rating/ranking, competitions, and so on.

Figure 16:
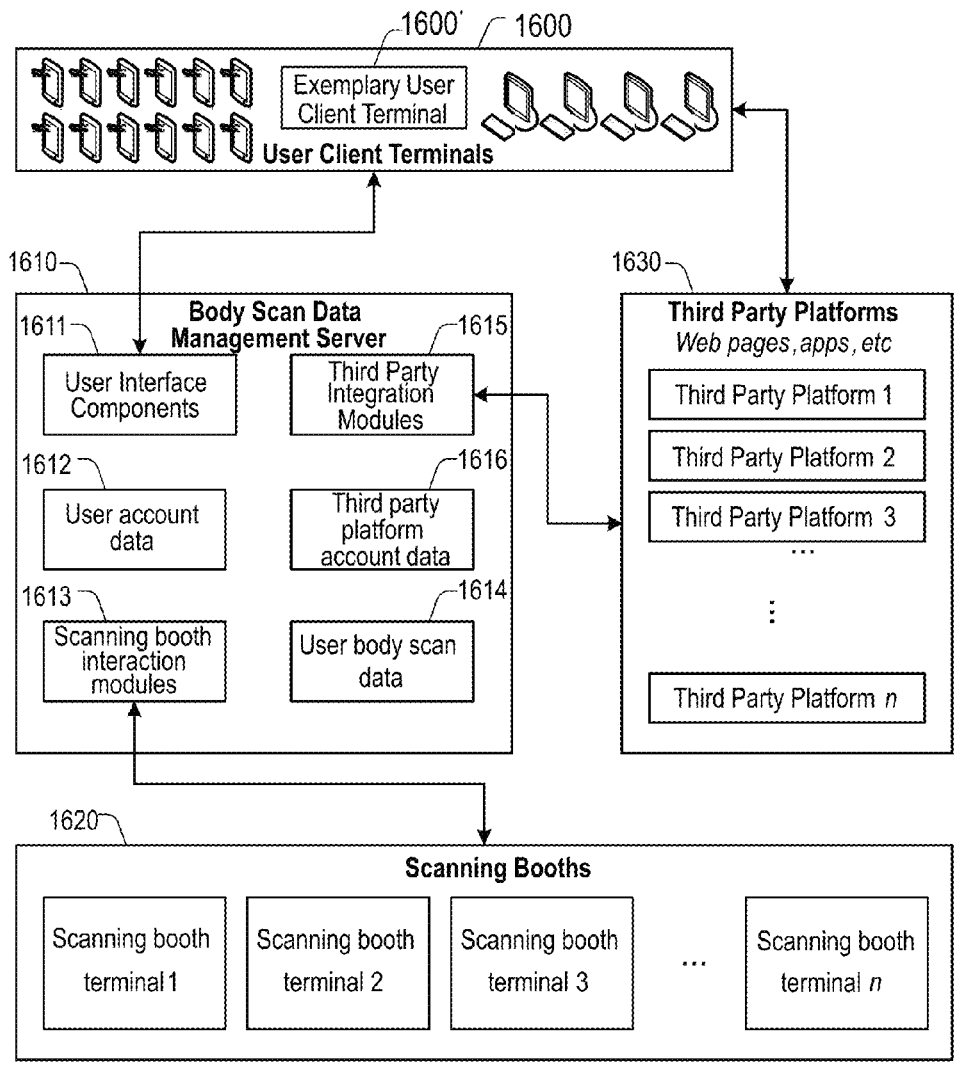
FIG. 16 illustrates a framework according to one embodiment.

FIG. 16 illustrates an overall framework according to one embodiment. Exemplary implementations of various components within this framework are described in more detail further below.

FIG. 16 centres around a body scan data management server 1610. This server may, in practical embodiments, be defined by one or more individual computing devices, optionally distributed over a number of physical locations. Server 1610 is configured to communicate with:

User client terminal 1600, which may include the likes of personal computers, notebooks, smartphones, tablets, gaming consoles, and the like. For example, these client terminals execute respective web browser applications, which enable local rendering of user interface components provided by a user interface component module 1611 of server 1610. These user interface components provide users with access to functionalities native to server 1610, which preferably includes account management (for example registration of a new account, and modification of existing account details, with user account data being maintained in a repository 1612) and in some cases scan management (for example modification of avatars, deletion of scan data, and so on).

Scanning booths 1620, which may include user-driven autonomous booths (such as those described below) and in some embodiments other scanning booths. Scanning booth interaction modules 1313 are responsible for enabling interaction between scanning booths 1620 and server 1610. This may include user account data management (for example where a user is enabled to register and/or login via a user interface provided at a scanning booth terminal), terminal maintenance (for example monitoring, downloading of software patches/updates), serving of advertising and/or promotional content, and so on.

Third party platforms 1630, which may include the likes of websites, proprietary software applications (including, but not limited to, mobile apps). Third party integration modules 1615 allow server 1610 to communicate with each of platforms 1630, preferably via a plurality of technological approaches. This may include widget based approaches (where code served by server 1601 is embedded within a web page provided by one of platforms 1630 and rendered at a given one of client terminals 1600, API-based approaches (whereby a third party platform communicates with and interacts with server 1610 via a predefined communications protocol), and other approaches.

Third party platform account data 1616 include data specific to each third party platform, thereby to allow either or both of (i) monetisation of services provided to those platforms on a monitored (for example per-use) basis; and (ii) maintaining platform-specific information (such as garment sizing data) thereby to allow tailored customisation of data and/or functionality provided via modules 1615.

Various examples of widgets and other functionalities provided by server 1610 to platforms 1630 are discussed in additional detail further below.

Autonomous User-Driven Scanning Overview

Embodiments described herein are primarily focussed on arrangements whereby scanning booths provide autonomous user-driven scanning. This means that a scanning booth provides user interface and user stimuli components which implement a logical process thereby to guide a user through a body-scanning procedure without intervention by a second human user. That is, a user is enabled to approach a booth, and have a user interface guide them through an entire scanning process, from login (or registration in the context of a non-registered user) through to scan completion (and in some embodiments avatar approval).

In general terms, a scanning booth configured to provide an autonomous user-driven scanning includes the following components:

- A user interface which provides a user interface thereby to enable a user to identify with the booth. This may include either or both of local registration (i.e. provision of personal information and the like thereby to create a new user account) and user login. A user login may include. providing user credentials, such as a username and password, defined subject to a previous local registration or a previous remote registration (using a terminal 1600 in communication with server 1610).
- A user interface and associated stimuli devices (for example visual and/or audible stimuli devices) configured to enable delivery of user instructions, thereby to enable a scan. These instructions include (i) preparation (for example clothing removal), (ii) stance and posture (for example positioning relative to defined feet positions and body position, preferably assisted by way of visual stimuli and automated feedback), and other such instructions. This allows automated scanning hardware (preferably in the form of infrared sensors) to collect body scan data from a body that is in a predefined desired stance and position. It will be appreciated that this greatly assists in analysis of collected measurements.
- Scanning components, such as infrared sensors, which are configured to make body scan measurements. These measurements are used thereby facilitate downstream functionalities, for example avatar generation.
- A user interface which guides a user through avatar generation and approval. Following approval, body scan data is transmitted to server 1610 thereby to be available for downstream use.

The user interfaces described above may be delivered by one or more screens, driven by one or more computing terminals.

Figure 1:
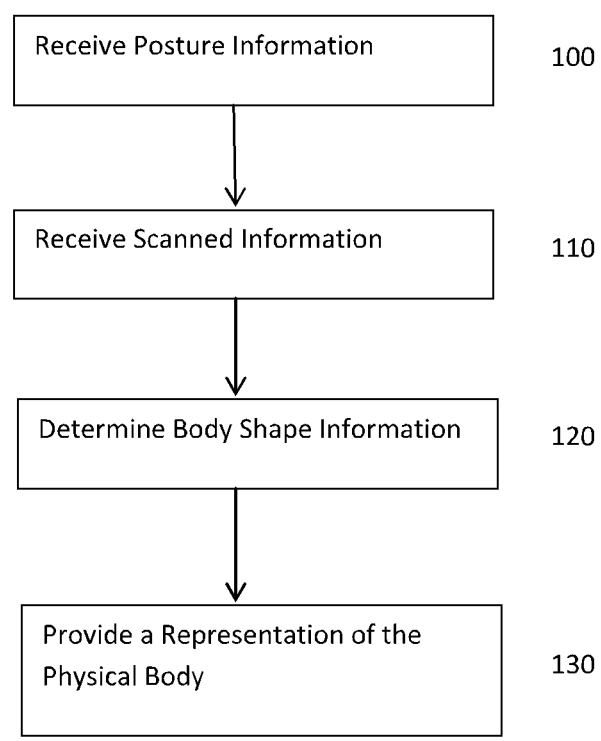
FIG. 1 is a flow diagram of an example method described herein.
Figure 2:
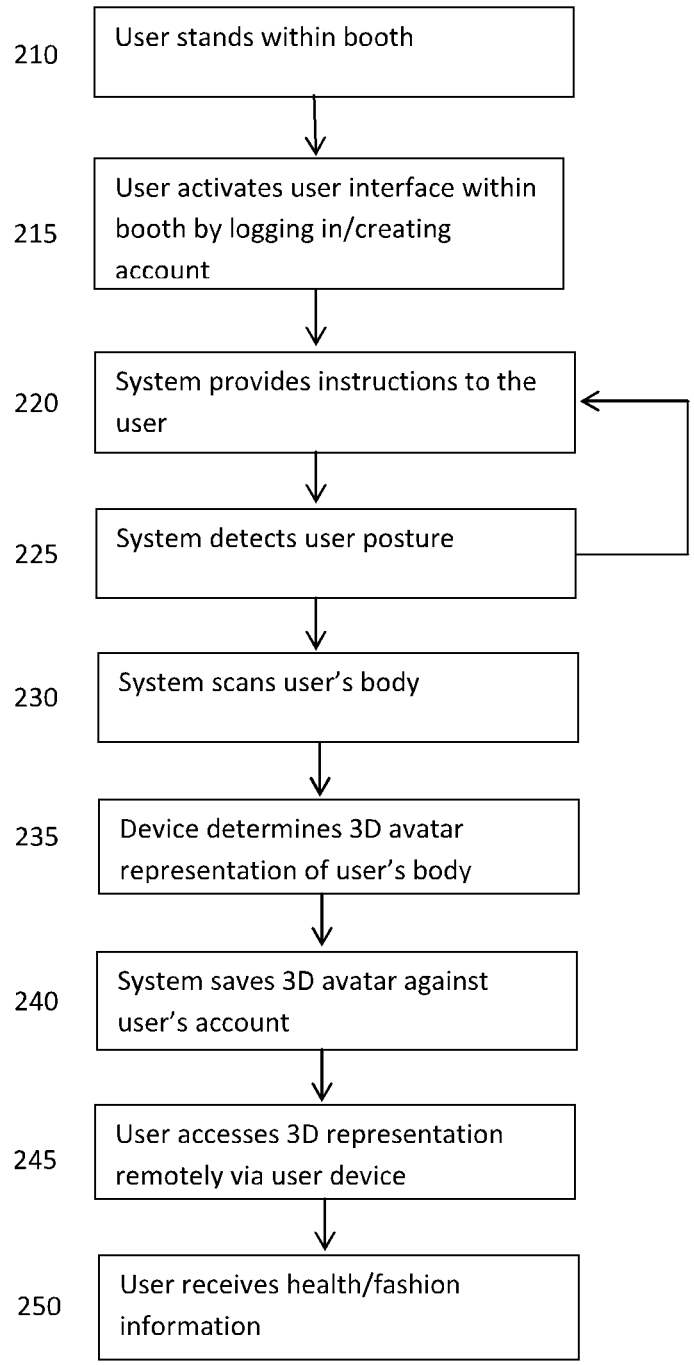
FIG. 2 is another flow diagram of an example method described herein.

FIGS. 1 and 2 show example processes for determining body shape information, associated with a physical body of a user. It will be appreciated that the processes of FIGS. 1 and 2 can be implemented by a system, which typically includes one or more processing systems. The system and the one or more processing systems are further described below.

FIG. 1 shows that at step 100, posture information can be received (notably, this is an optional step and can include receiving user stance or standing position information), at step 110, scanned information can be received and at step 120, body shape information can be determined in accordance with the received scanned information. At step 130, a representation of the physical body can be provided.

In the example of FIG. 2, at step 210, a user stands within a booth and at step 215, the user can activate a user interface within the booth by logging in or creating a user account. At step 220, the system can provide instructions to the user and at step 225, the system can detect the user's posture (and/or standing position). Accordingly, if the user is required to amend their stance (i.e. foot position, body direction, etc.), the system can provide further instructions and the processes can loop back from step 225 back to step 220. Posture correction steps may be repeated later in the process, for example based on analysis of scan data (for example resulting in re-scanning subject to posture correction). Analysis of posture includes analysis of standing position. That is, there is assessment of both body location (for example standing location, standing direction, foot position, etc.) and body pose (for example spine alignment, limb positions, shoulder position, etc.).

At step 230, the system can scan the user's body and at step 235, the system can determine/generate a three dimensional (3D) avatar representation of the user's body. The 3D representation can be provided to the user as one or more images. At step 240, the system can save the 3D avatar representation against the user's account. Thus, the avatar (and/or associated measurement data) can be saved either locally with a data store or database associated with the processing system positioned within the booth, or alternatively, in a cloud or any other form of data store. Accordingly, at step 245, the user can access their 3D representation via a user device and at step 250, the user can receive health and or fashion information/recommendation in accordance with the scanned information (which is further described below).

Figure 3:
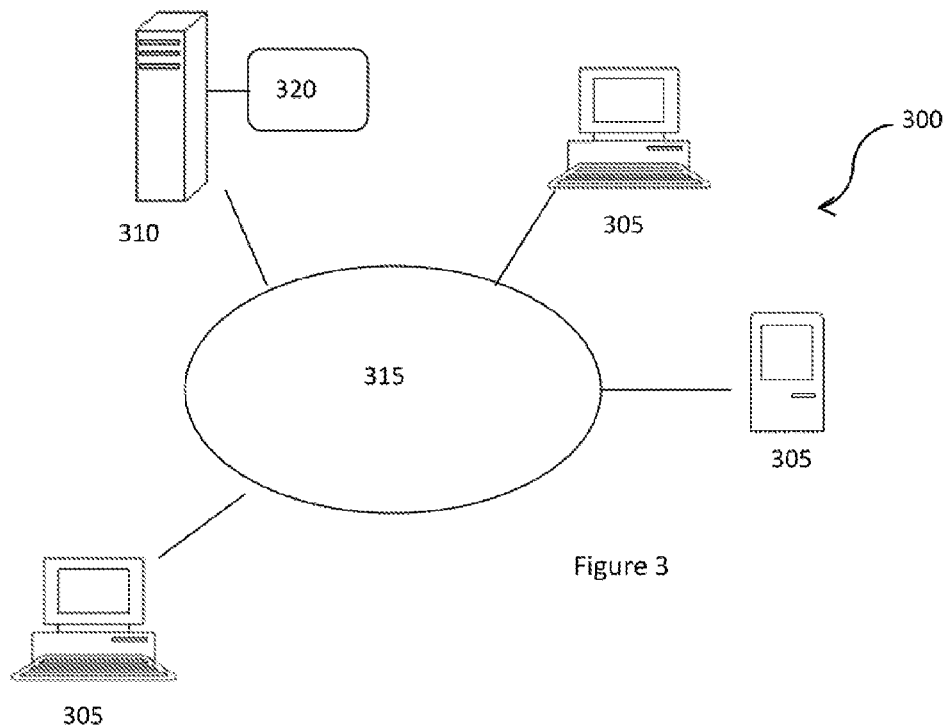
FIG. 3 is a schematic representation of an example system which can be used to implement the methods described herein.

As discussed, the processes of FIGS. 1 and 2 (and other processes described herein) can be implemented by one or more processing systems. FIG. 3, shows an example of a distributed network 300, which can include a plurality of computer/processing systems 305/310, connected via a network 315.

In this particular example, the processing system 310 can implement the processes outlined in FIGS. 1 and 2, where a user can have access to the process described herein via a main or server processing system at 310 or via any other form of user terminal/device 305. The main processing system 310 is in this example, connected to a database or data store 320. However, it will be appreciated that the data store can be any form of device/system which can store data or include a database such as any form of memory, cache, or data cloud.

Notably, the processing systems 310/305 can be any form of processing systems including a desktop or server system, a laptop, tablet or mobile telecommunication device with or without their own data stores and/or with or without access to external data stores. Additionally, the processing systems 210/205 can include display devices such as monitors or the like, and other input/output devices such as a mouse, keyboard, infrared or Bluetooth detection capabilities, cameras, or the like.

It will also be appreciated by persons skilled in the art that the network 315 can be any type of Internet, Intranet, WAN, LAN, or the like. Furthermore, computer/processing systems 305/310 can be any type of user processing system, server system, or the like.

Figure 4:
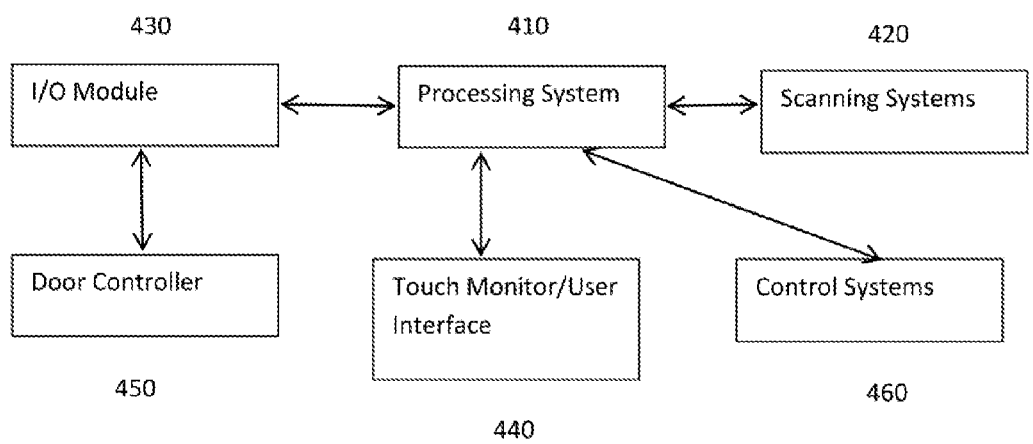
FIG. 4 is a schematic representation of an example system which can be used to implement the methods described herein.

An example of a system 400 (which can be used to implement the processes described herein), including a processing system (which is typically the processing system 310), is shown in FIG. 4. In this particular example, the processing system 410 communicates with scanning systems 420 for scanning the user's body, control systems 460 for controlling various operations (such as, for example operations associated with a booth of the system, as described below) and Input/Output modules or systems at 430 for controlling any form of input/output into and out of the processing system 410, such as, for example, control of the door of a booth (further described below) at 450. The processing system 410 can also be in communication with a touch monitor or user interface 440, for communicating with the user accordingly.

Accordingly, there is provided herein a system for determining body shape information associated with a physical body of a user, where the system typically includes a processing system (such as the processing system 210/410), and a scanning system 420. The scanning system 420 is typically for scanning the physical body of the user, where the scanning system 420 is configured to communicate with the processing system 410 to provide scanned information to the processing system 410. The processing system 410 can then receive the scanned information and determine body shape information associated with the scanned information.

Thus, for example, the scanning system 420 can include one or more scanning cameras for scanning the physical body, where the scanned information provided by the one or more cameras can include basic body measurements as obtained by the one or more scanning cameras (not shown).

Notably, as well as receiving scanned information, in order to determine body shape information, the system can also determine posture information, associated with the user's posture, and weight information, associated with the user's weight, and height information, associated with the user's height. In one particular example, posture information may not be included in the generation of the 3D representation, and is only used as a signal to start body scanning.

Thus, the system can provide a representation of the user's physical body, to the user. The representation is typically generated based on the body shape information. In one particular example, the representation is a three-dimensional (3D) avatar of the physical body.

It will be appreciated that although a 3D avatar or image representation of the user's body can be provided to the user, the representation of the user's body can also be provided in various different forms. Thus, for example, a body can be described and presented to the user using numerical data eg: Weight XX kg, Height XX cm, Chest XX cm, Waist XX cm, Hip XX cm and so on (hundreds of body's measurements are calculated and stored by the system). Furthermore body shape can be presented to the user using a body descriptor such as, a "fashion classification" (for example "inverted triangle with long legs, short torso", "hourglass with balanced legs and torso", etc.). These are further described below. Thus, typically, the representation is in proportion to/representative of the physical body and is representative of the height, weight, shape, and/or outline of the physical body.

According to one particular example, the processing system 410 and the scanning system 420 can be provided in a booth, where the user can enter the booth in order to obtain a representation of their body from the system. It will be appreciated that the booth is typically at a height taller than the height of the user standing therein.

Furthermore, the booth can also include a number of features such as a standing area positioned on the floor of the booth, where the standing area can be indicative of where the user needs to stand for scanning, and a user interface which is typically in communication with the user for providing the user with information. Thus for example, the user interface can provide the user with any one or a combination of scanning instructions, a representation of the physical body on a screen or display, a health, goal, progress or exercise report, and/or a fashion recommendation. The features of the booth and user interface are further described below.

Exemplary Booth and User Interface

Figure 5:
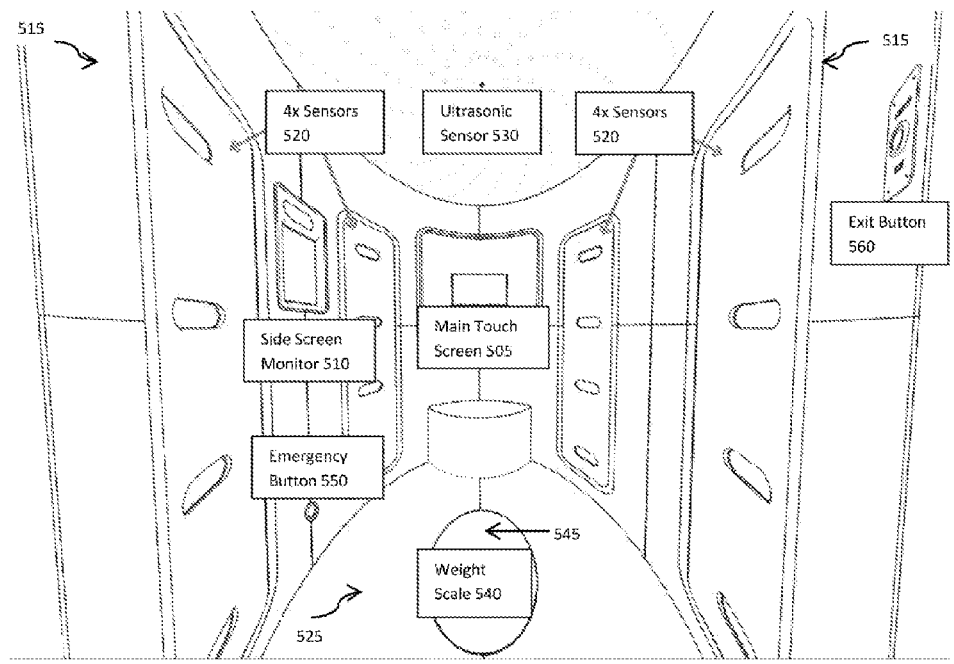
FIG. 5 is a schematic representation of an example booth which can be used to give effect to the methods and systems described herein.

FIG. 5 shows an example interior of a booth or module 500 for scanning a user's body. In this particular example, the booth includes a main touch screen or user interface at 505 as well as a side screen monitor at 510. The booth may be of various shapes, for example circular/cylindrical so that the walls of the booth 515 surround the user, once the user stands therein, or of square/rectangular base. It is preferred that the booth is shaped thereby to enable a 360 degree scan of the user's body, as the scanner can be placed strategically around the walls 515. Thus, in this particular example, there is provided one or more scanners 520, placed significantly around the walls 515, and the booth may also be entirely enclosed when scanning. In preferred embodiments, the booth is entirely enclosed during operation, including a ceiling.

FIG. 5 also shows that booth can include, within or on a floor section 525 a weight scale 540, for measuring the weight of the user. The weight scale 540 can be located in a standing area 545, which is where a user would typically stand in order to be scanned. The booth 500 may also include an ultrasonic sensor 530 for measuring the height of the user.

Figure 6:
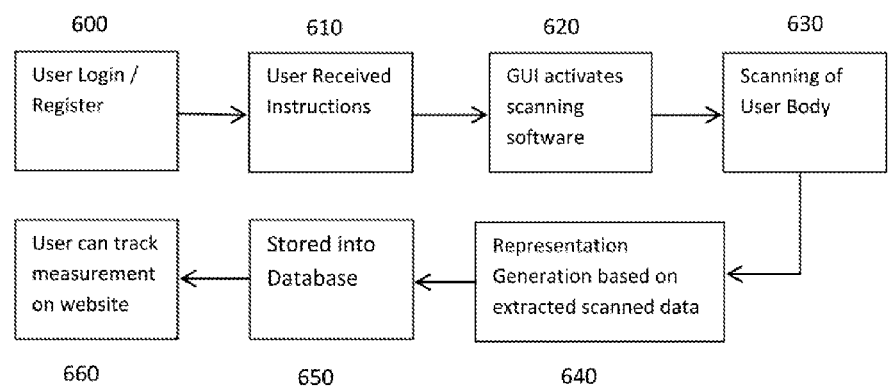
FIG. 6 is a flow diagram of another example method described herein.

FIG. 6 shows an example of a process which can be performed when a user is in a booth. Thus, for example, a user can enter the booth by interacting with an opening mechanism (for example pressing a touch screen door), which is typically connected to one or more processing systems within the booth. In some cases the booth is inherently open when vacant. In some cases a display (for example an LCD display) external f the booth indicates whether the both is vacant or occupied. The touch screen door is connected via an I/O module to the one or more processing systems.

Thus, the user enters the booth and starts by interacting with a Graphical User Interface (GUI) on a display in the booth, otherwise referred to herein as the user interface. The interaction can be via a main touch screen computer/processing system. Typically, the door of the booth is locked once the GUI has started and the scanning system is also started. The locking action can be implemented via an electro-magnetic lock, although other lock systems may be applicable.

The user is typically requested, via the user interface to register or log into their pre-registered user profile, which is shown at step 600 of FIG. 6. A processing system within the booth is able to validate the user log in by comparing the data entered by the user to a database of known users. If a user needs to register on the system, they would typically need to enter in their user details, such as, for example, their name and contact information as well as birth and gender details (for health report generation, as discussed below). The user is also associated with a password (which may be user defined or automatically defined, and in the latter case it may be subsequently modifiable by the user).

Once the user has proceeded passed the logging in process, the user may be shown an instruction video at step 610. The user may also be requested to remove clothing (in some cases all clothing) and store these in an area provided for within the booth (for example hung on hooks that are provided within the booth, a region for containing footwear and other garments, and so on). Clothing is typically removed to obtain a more accurate scan. Handles, a seating area, clothing hooks, and the like are preferably provided thereby to assist a user in comfortably undressing and dressing in the enclosed space of the booth.

Instructions can be provided to the user via the user interface in relation to where to stand and how to stand (preferably in combination with markings which define a predetermined foot position on the floor of the booth). Furthermore, the system can also include the use of posture recognition, where once the correct posture is detected, the user is then asked to stand still for a time period (which, in one example, is 20 seconds) for the scanning to occur. Thus, as shown at step 620 the GUI's interaction with the user can activate scanning software, where at step 630 the user's body is scanned.

Typically, during the scan process, one or more lights within the booth may dim automatically, the dimming being controlled by one or more processing systems within the booth. Other stimuli may be used to indicate commencement of scanning.

Thus, at step 640 a representation, which can be one or more image representations of the user's body is generated based on the extracted scanned data. This data, as discussed (below) can be stored into a database at step 650 and the user can then track their measurements on a website at 660.

It will further be appreciated that the booth can include many other features, for example, a smoke alarm or other emergency alarms, emergency switches which can allow the user to exit the system at any point, and systems for automatically unlocking the booth, if the user has been inactive for a period of time. Examples of emergency and exit buttons are shown at 550 and 560 in FIG. 5, respectively. Additional optional features/functionalities include: remote monitoring and/or maintenance capabilities, monitoring devices which record and report on all booth hardware activity, and various timers (for example to control unlocking of doors, restarting of GUIs and/or hardware components, etc.).

As discussed above, the one or more processing systems 410 within the booth can be connected to a network such as the Internet, or the like. The network connection can be used for uploading the user's scan onto a user database, which can be hosted remotely from the booth. Thus, for example, if there is no database connection, the user may still be able to scan and their data can be stored locally and updated when connectivity is restored. Accordingly, the user can log online onto a platform remotely (such as via the user devices 305, for example) and can also be asked to confirm the scan, prior to the scan being added to their user profile.

It will further be appreciated that information in relation to the user profile (including one or more representations of the user's body) can be stored in a data store such as the example data store 320 shown in FIG. 3 which can be a cloud-based storage system, a database, or any form of memory device that is able to store data/information.

Accordingly, the system discussed herein can provide interaction with the user, and provide the user with their body representation via a number of user interfaces. Thus, for example, the user interface within the booth (as shown at 505 and 510) can provide the user with various information, or alternatively, the information can be provided to the user via the distributed network in FIG. 3, where the user can remotely access information via a user device, such as the user's smart phone or mobile processing system.

Exemplary Application: Fashion

According to another particular example, the systems and methods described herein can be used to automatically generate recommendations to a user in relation to fashion.

An example of a method for providing a fashion recommendation, typically by a processing system, is shown in FIG. 7.

Figure 7A:
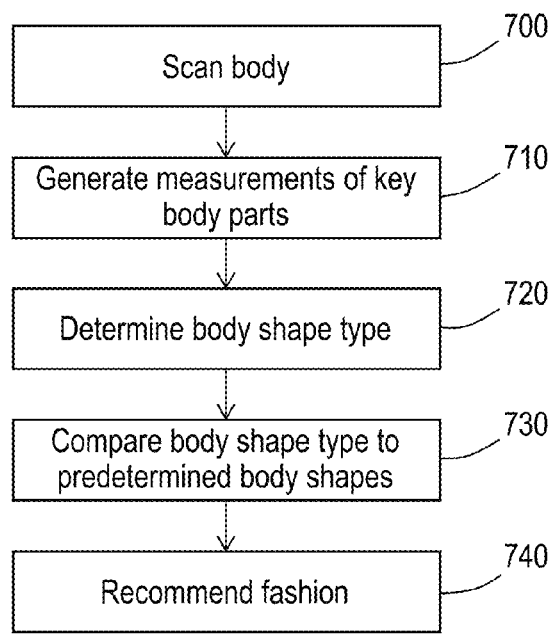
FIG. 7A is another flow diagram of an example method described herein.

In FIG. 7A, at step 700 the system described herein performs a scan of the user's body. At step 710 the scanned information is used to generate measurements associated with key body parts and at step 720 a body shape type is determined. Notably, as discussed below, the measurement can include one or more horizontal measurements and/or vertical measurements. At step 730, the determined body shape type is compared to pre-determined body shapes, which are typically stored in a data store, and at step 740, in accordance with the comparison, one or more fashion choices can be determined and particular fashion choices can be recommended to the user, based on their body type. Notably, if a user's body shape changes, the system is able to provide updated recommendations accordingly. Furthermore, as fashion changes, the system is able to provide updated recommendations accordingly.

Figure 7B:
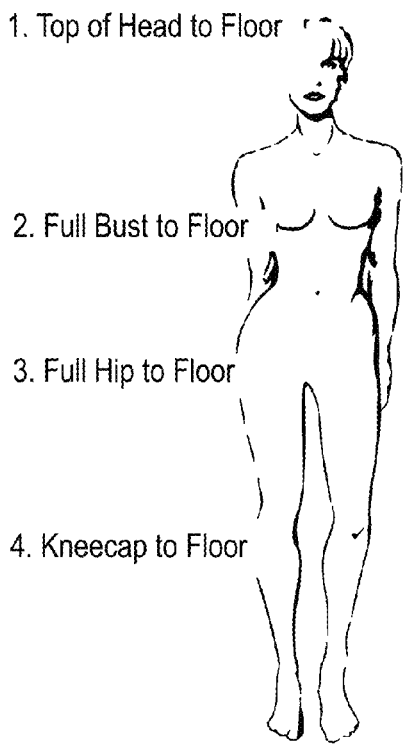
FIG. 7B is a schematic representation of a body which can be measured, in accordance with the systems and methods described herein.

FIG. 7B shows an example of user's body with key body parts which can have measurements associated therewith. Thus, the example of FIG. 7B shows four vertical measurements which can be determined including (but not limited to) measurements representing the heights of: the top of the head to the floor, the full bust to the floor, and the full hip to the floor and the knee to the floor. These can be referred to as vertical measurements associated with the user's body.

Accordingly, a shape analysis can be performed which includes considering both horizontal measurements (that is, measurements across the body at different horizontal lines) and vertical body length proportions.

From the horizontal and/or the vertical measurements it can be determined what body shape type the user has. Thus, for example, the user's body can be classified as having a particular body type including (but not limited to) an hourglass-shaped body type, a balanced body type (where, for example, the body is the same height from the midline, as opposed to long legs and short torso or vice versa), an inverted triangle type, a pear-shaped type, and the like. Notably, each or both of the horizontal and/or vertical measurements can be used to determine the body type. Furthermore, the body shapes may vary depending on the sex of the user.

Thus, once the body type has been determined, the user's body measurements and/or shape style recommendation (horizontal and/or vertical) can be matched with pre-determined body measurements for each fashion label and determining a fashion recommendation including the size, fit and style for a user's body type and measurements. Notably, determining one or more fashion choices can include accessing fashion item information associated with a fashion item (which can be stored on any data store, including a third party data store), where the fashion item information includes item measurement information. Fashion item information can include the item size, although the measurement information is typically more detailed than the size of the item and can include same measurement information as of the user, such as fit points, which are discussed further below.

It will be appreciated that in further embodiments alternate measurement approaches may be adopted.

In yet a further embodiment, the system and method described herein can provide sizing recommendation in accordance with data collected from different fashion labels. Thus, for example, data collected in respect of various types of clothing at specific fashion labels can be used to identify one or more fit points on a particular item of clothing.

Thus, once measurements on a user's body are determined, the measurements can be compared to the pre-determined fit points on various types of clothing and a recommendation can be provided accordingly. Typically, each fit point is uniquely associated with a body measurement which has been pre-determined and stored in a data store. Furthermore, there is no limit to the number of fit points which can be used, as it will be appreciated, the ability to add more points can significantly improve the knowledge of fit and sizing for users.

Additionally, in this particular example, a substantial match between the fit points of the physical body and the pre-determined fit points associated with a fashion choice can be typically required to then recommend the fashion choice.

Thus, the system and method described herein can provide the most suitable size for the user, in relation to an item of clothing.

According to yet a further embodiment, the closest point of reference for each point of fit can be calculated. Thus for example, if it has been determined that a user's waist is 30 cm, the system and method described herein searches for the closest size to 30 cm and provides a recommendation accordingly. If the measurement is higher or lower, the system can display to the user that the fitting is too tight or too loose. However, typically, within a certain margin of error, there will be no message displayed (for example, within 1 cm).

According to one particular example, the system can store information in relation to a specific fashion item including a brand identifier associated with the item, item type, and item measurements. Example item types can include upper body wear, lower body wear and/or outerwear. Additionally, item measurement details can include (and not limited to) Bust: BustGirth, Waist: WaistGirth, Hip: HipGirth, Inseam Length: InseamLeft, Neck: NeckBaseGirth, and Chest: ChestGirth.

According to yet a further embodiment, the system and method described herein provides an online retailer with an opportunity to be a part of the distributed system, with access to the system and method described herein. Thus, for example, a user using an online retailer's website or Internet platform (which can include a mobile site or any form of site) can be provided with sizing recommendations by the online retailer, in relation to the user's scanned information as stored and accessed by the user, via a portal on the online retailers' internet platform. In this example, it will be appreciated that the recommendation can be displayed to the user without the user having to leave the retailers site at any point of time.

Example Application: Health and Exercise

As discussed, a user can use a user device, such as the user's mobile telecommunication device or a third party processing system, or the like, to access the generated representation. Thus, for example, the user may have access via a remote user interface to access their profile information and other data which has been stored against their user profile.

An example of data can include a personalised health report including fat content, which can also be sent to the user via any form of electronic communication.

The health and exercise application can also include a goal generator which can be a motivational tool for users to keep track of their health goals, to aid the user to stay on a particular exercise/health plan.

Thus, users may be able to customise their goals based on data that is available on the system, which is able to use the user's goals and personal data to encourage users to meet their goals.

In one example, by using scanned information and body shape information over time, the system can identify weaknesses and strengths of the user.

Furthermore, the system can be configured to provide the user with the ability to share their personal scan data with their friends or a pre-defined group of other users, to get more motivation as they achieve their goals. Thus, for example, the user can gain points as they achieve certain goals and unlock certain rewards.

Additionally, the user can also be provided with a customised exercise plan based on the scanned data, goal generator, and or the user's input.

Furthermore, the user can also log their progress on the exercise plan and move up to different levels as they progress.

In yet a further embodiment, the progress of the user can be tracked for each major body part of the user over time on a graphical user interface.

According to one particular example, the system and method described herein can generate a health report with health indicators being determined by considering a number of different factors for each user, where the factors are typically derived from scanning the user's body. Thus, for example, the health report can include (and not limited to) information in relation to the user's Body-Mass Index (BMI), waist/hip ratio, fat content, waist circumference, waist/height ratio, weight, height, chest, bust, upper waist, waist, left/right bicep, left/right thigh, and left/right calf measurements. Examples of these measurements are given in the tables below:

Example BMI=weight/(height*0.01*height*0.01)

|  |  |
|---|---|
| <18.5 | Underweight |
| 18.5 to 24.9 | Healthy |
| 25 to 29.9 | Overweight |
| 30+ | Obese |

Example Formula for Waist/hip ratio is:

Waist/hip ratio=waist girth/hip girth

Male

|  |  |
|---|---|
| <0.85 | Excellent |
| 0.85 to 0.90 | Good |
| 0.90 to 0.95 | Average |
| 0.95 to 1 | High |
| 1+ | Extreme |

Female

|  |  |
|---|---|
| <0.75 | Excellent |
| 0.75 to 0.80 | Good |
| 0.80 to 0.85 | Average |
| 0.85 to 0.90 | High |
| 0.90+ | Extreme |

Example Formula for Fat content is:

Male Fat content=100*(−98.42+(4.15*upperwaist)−(0.082*weight))/(weight)

|  |  |
|---|---|
| <2 | Under essential fat |
| 2 to 6 | Essential fat |
| 6 to 14 | Athletes |
| 14 to 18 | Fitness |
| 18 to 26 | Acceptable |
| 26+ | Obese |

Example Female Fat content=100*(−76.76+(4.15*upperwaist)−(0.082*weight))/(weight)

| | |
|---|---|
| <10 | Under essential fat |
| 10 to 13 | Essential fat |
| 13 to 21 | Athletes |
| 21 to 24 | Fitness |
| 24 to 32 | Acceptable |
| 32+ | Obese |

Example Formula for Waist circumference is:

| | |
|---|---|
| Waist girth <94 | No risk |
| Waist girth between 94 to 102 | At risk |
| Waist girth 102+ | High risk |

Example Formula for Waist/height ratio is:

Waist/Height ratio=waist girth/height/100

Male

| | |
|---|---|
| <35 | Abnormally Slim |
| 35 to 43 | Extremely slim |
| 43 to 46 | Slender |
| 46 to 53 | Healthy |
| 53 to 58 | Overweight |
| 58+ | Obese |

Female

| | |
|---|---|
| <36 | Abnormally Slim |
| 36 to 42 | Extremely slim |
| 42 to 46 | Slender |
| 46 to 49 | Healthy |
| 49 to 54 | Overweight |
| 54+ | Obese |

Figure 12A:
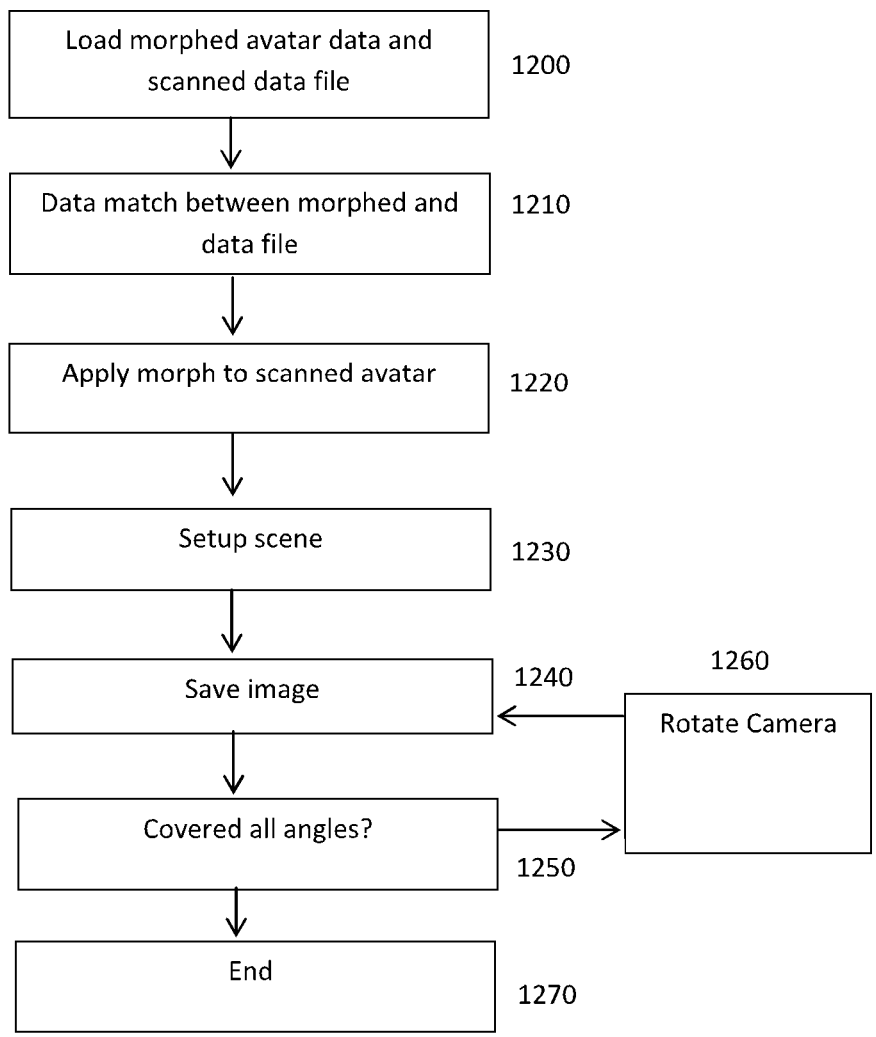
FIG. 12A is another flow diagram of a further embodiment of a method as described herein.
Figure 12B:
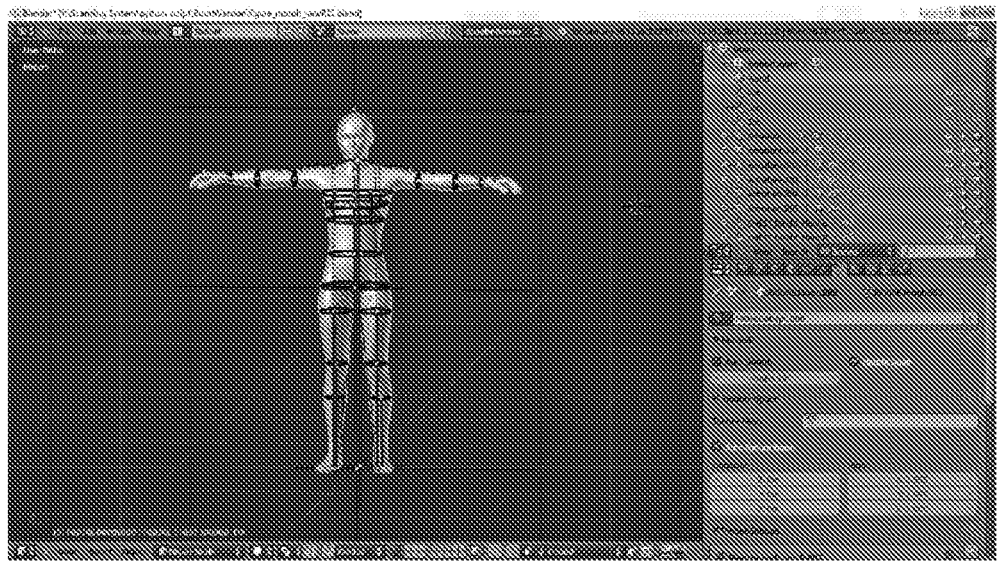
Figure 12C:
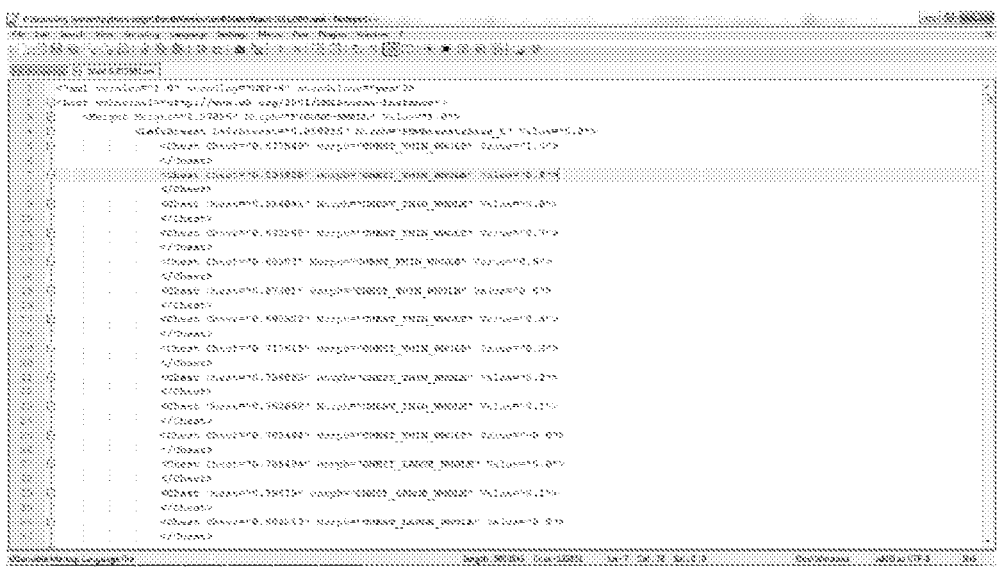
Figure 12F:
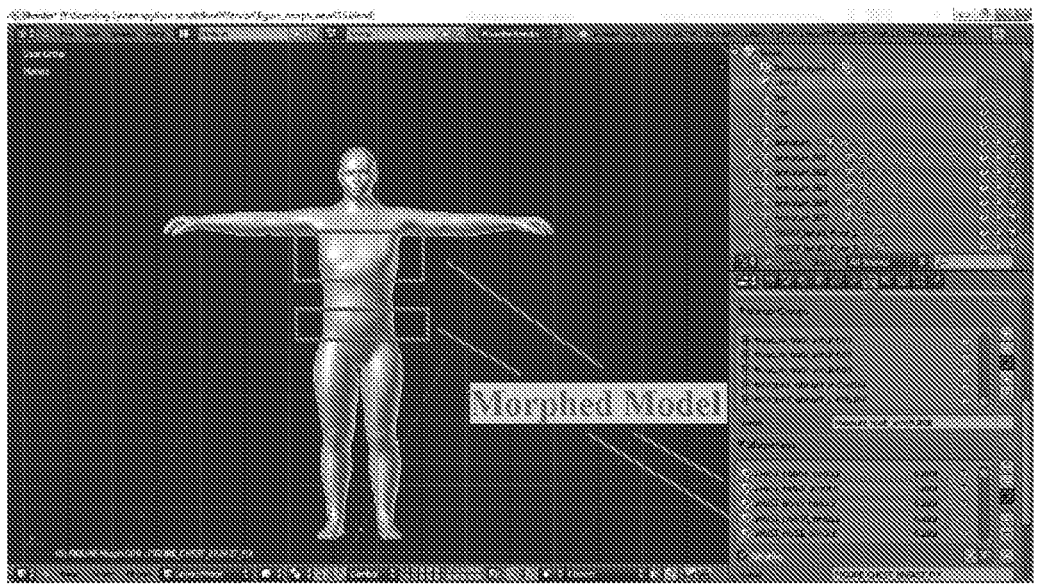
Figure 12G:
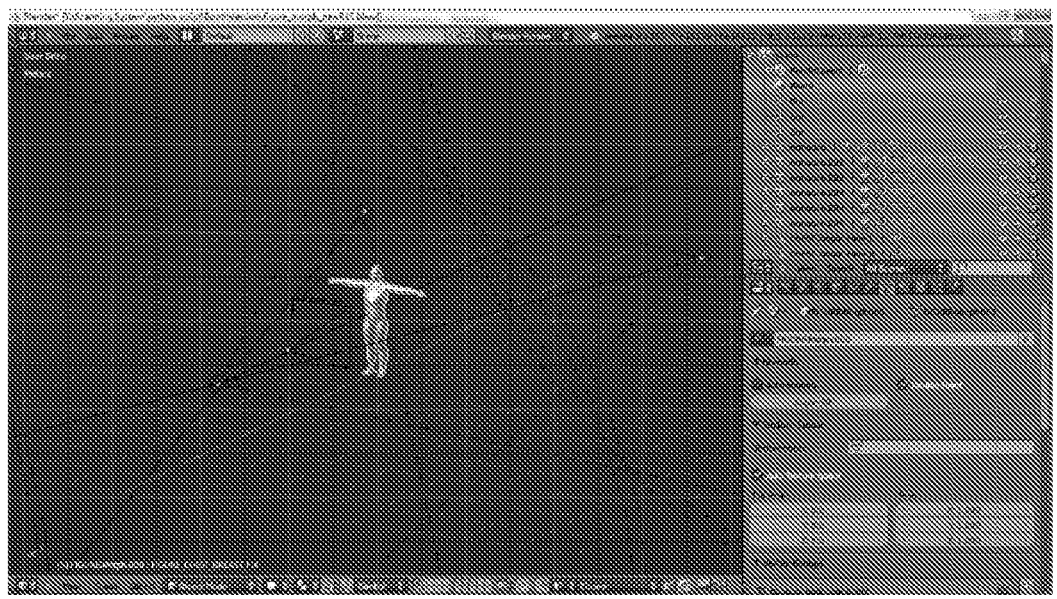
Figure 12H:
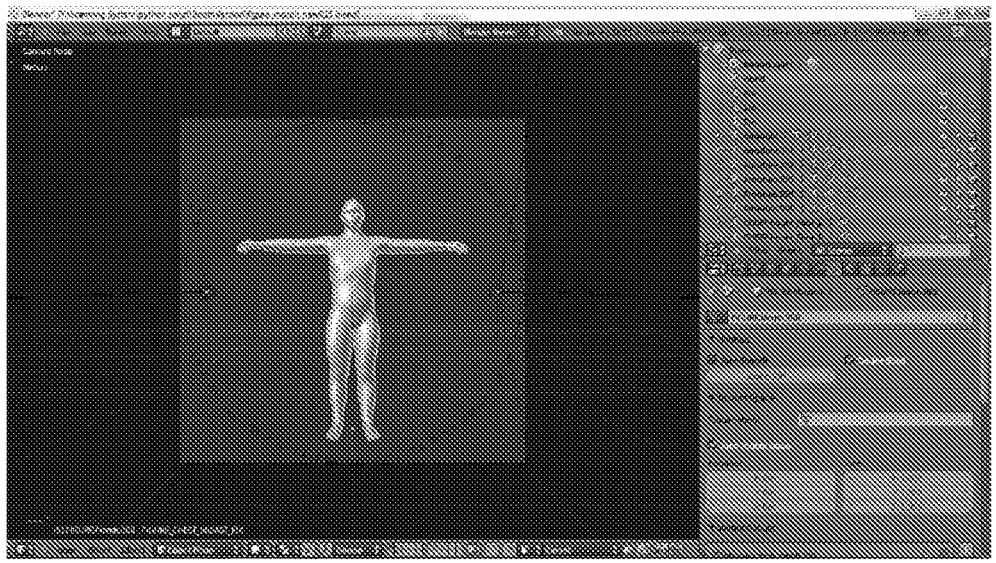
Figure 12I:
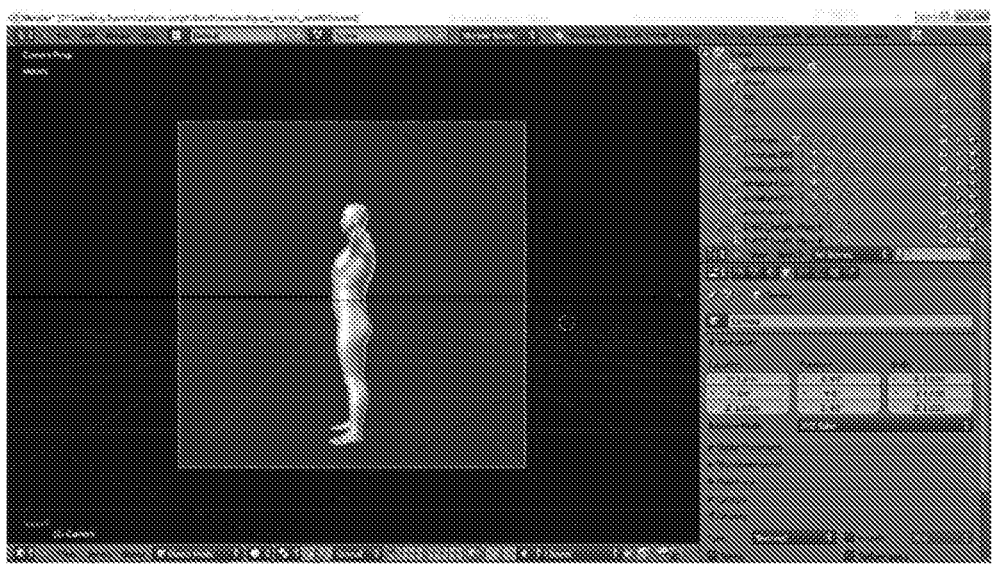
Figures 12J, 13A:
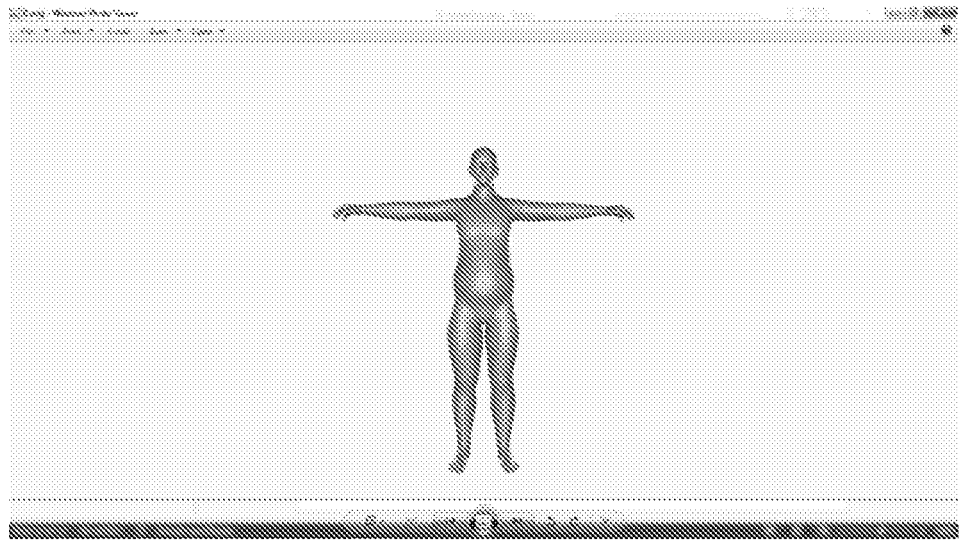
Figure 13B:
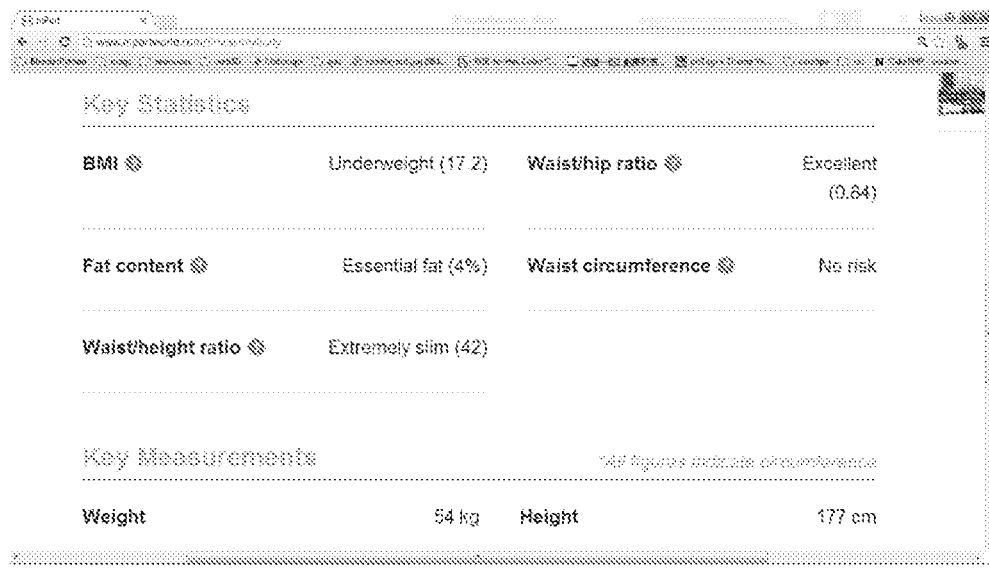

FIGS. 13A and 13B show examples of health reports which can be provided to the user, via a display (the display being a part of the booth or a part of a remote user device). In particular, FIG. 13A shows an example of a report showing the key measurements as derived from the scanned body of the user. FIG. 13B shows an example of a health report with key statistics, which can also be derived from the scanned body of the user.

Figure 14A:
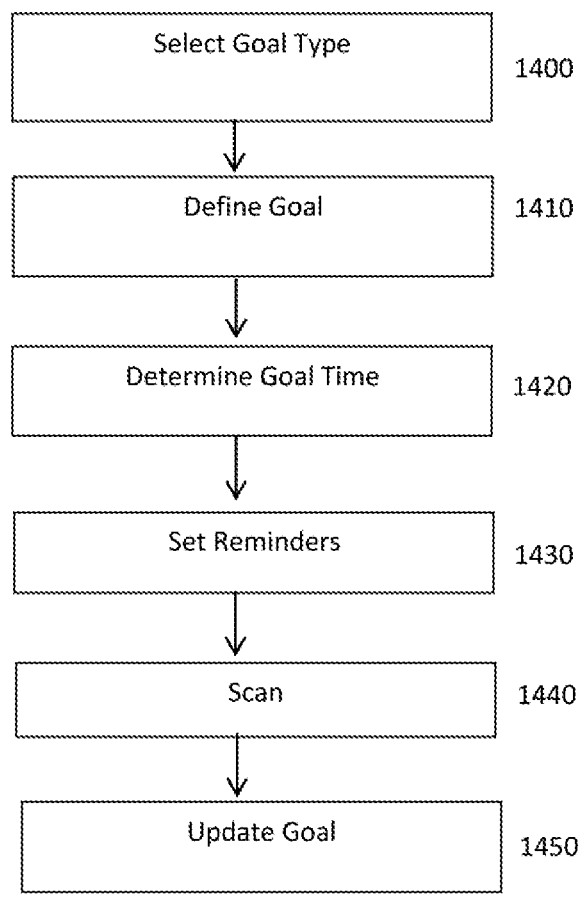
FIG. 14A is a flow diagram of a further embodiment of a method as described herein. and, FIG. 14B to FIG. 15I are schematic representations of example screen shots showing an application of the system and method described herein.

According to yet a further embodiment application of the systems and methods described herein, FIG. 14A shows an example of a process for generating one or more goals such as health/fitness goals, and tracking the one or more goals.

Figure 14B:
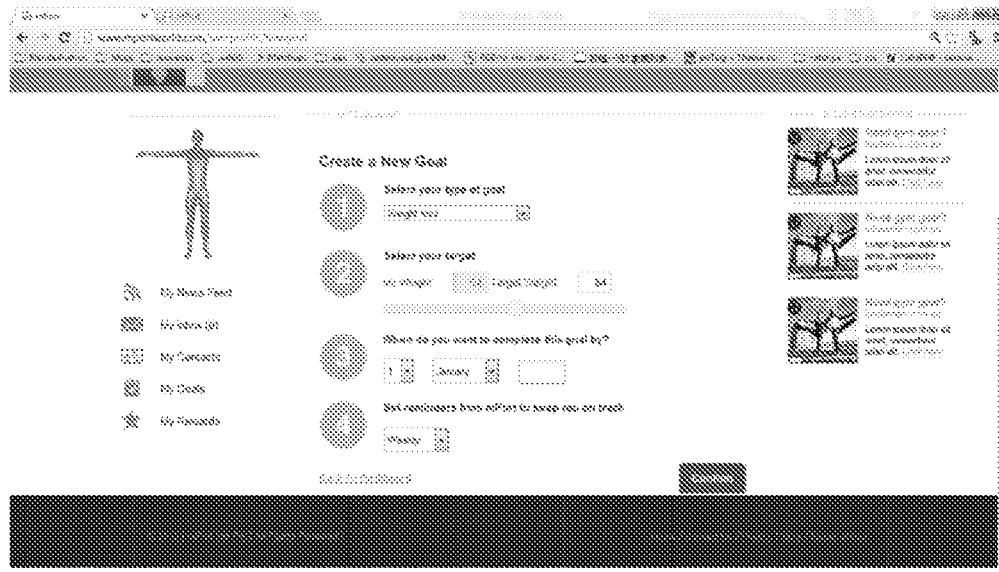

In this particular example, a user may be able to access data stored by the system and create a user profile which allows the user to start entering in goals, associated with their user profile. Thus, at step 1400 a user may select a goal type, such as for example, weight loss, gain fitness, or the like. At step 1410, the user can further define the goal, such as for example, submit to the system how much weight they wish to lose. At step 1420, the user can determine a goal time. That is, when they wish to complete the goal by and at step 1430, the user can set one or more reminders so that the system can help the user to keep track of their goal. An example of a display which can allow a user to set up a goal is shown at FIG. 14B. At step 1440, the user can get one or more scans of their body via the system as described herein, where the system can automatically update the user's goal tracking at step 1450.

Accordingly, the method can include a processing system being configured to receive user goal information, receive updated scanned information and track user goals information accordingly.

Figure 14C:
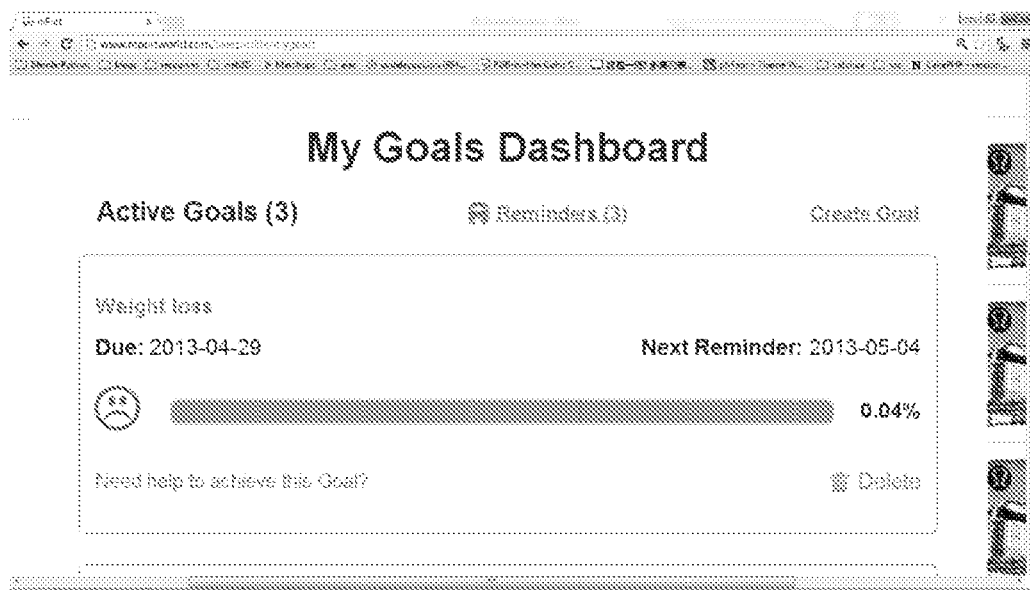

Thus, for example, once a user confirms their goal, the system can generate a goal dashboard where the user is displayed one or more summaries for their current goals. An example goals dashboard is shown at FIG. 14C. The dashboard can be automatically updated and messages of encouragement can be sent to the user via any communication means, as the user achieves certain goals.

Figure 15A:
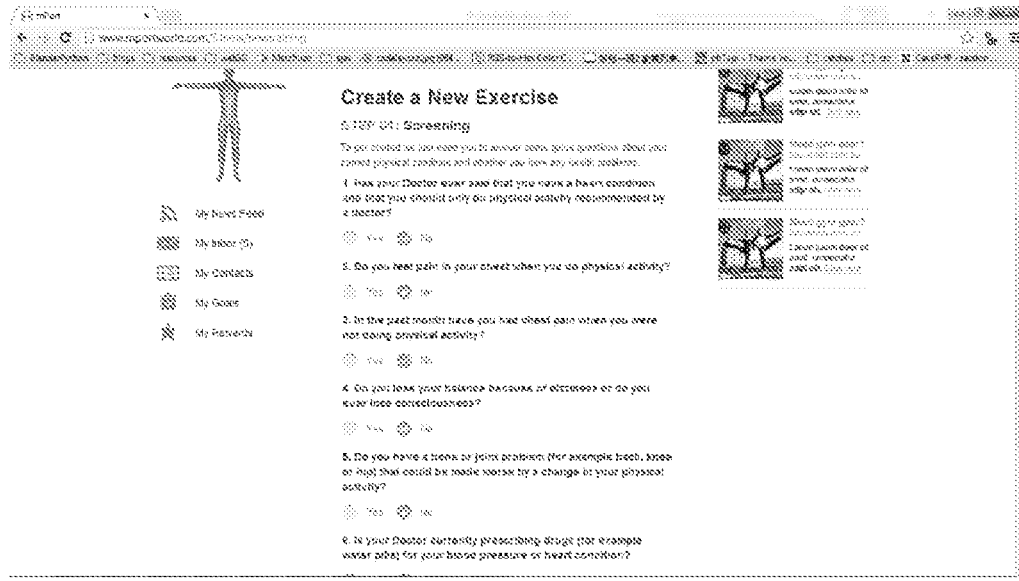
Figure 15B:
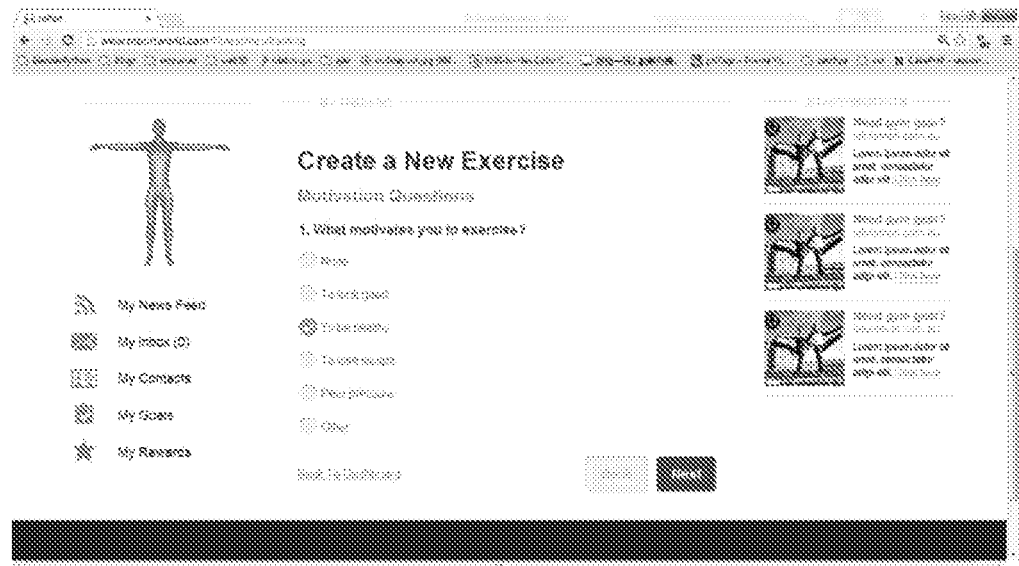
Figure 15C:
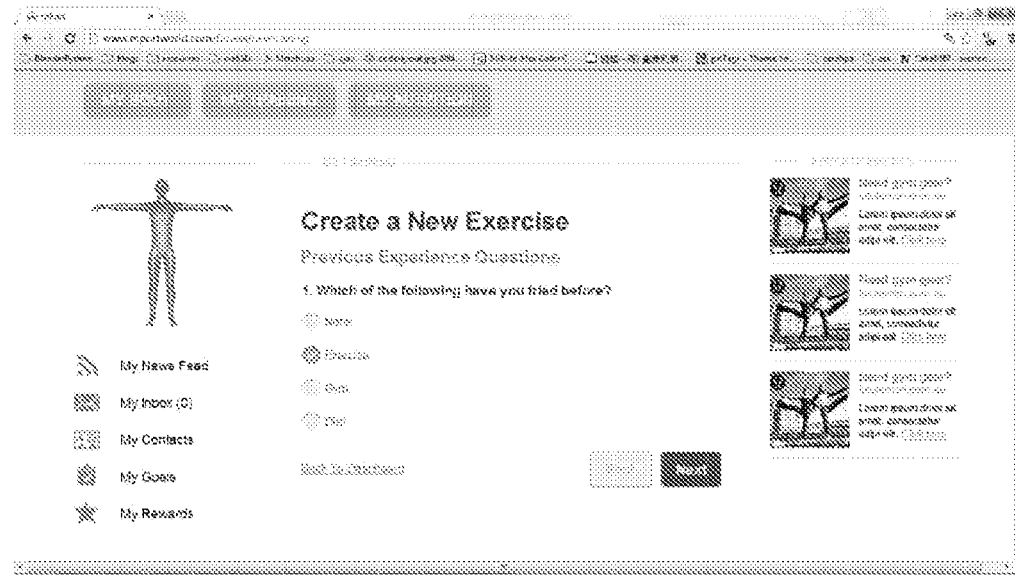
Figure 15D:
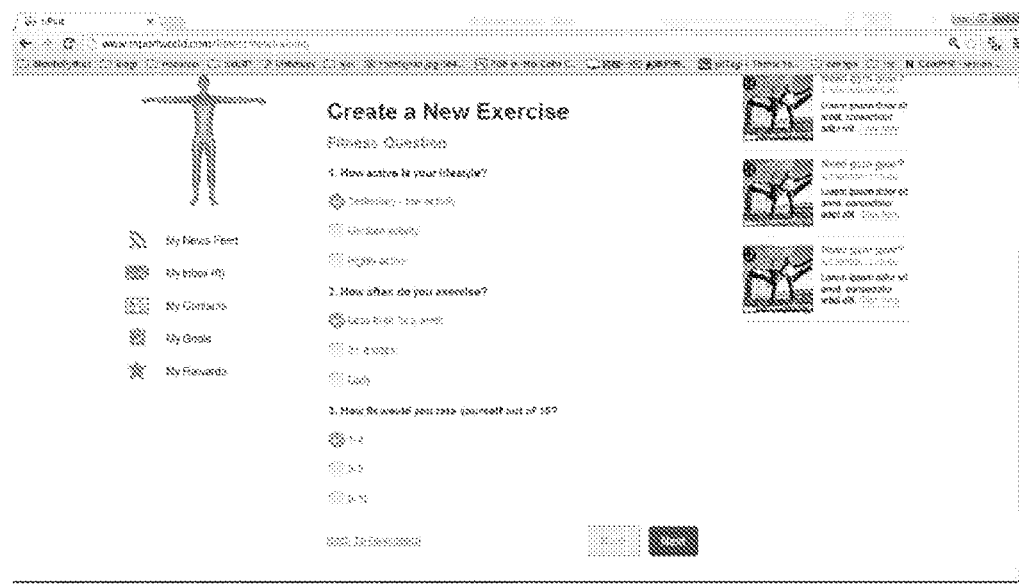
Figure 15E:
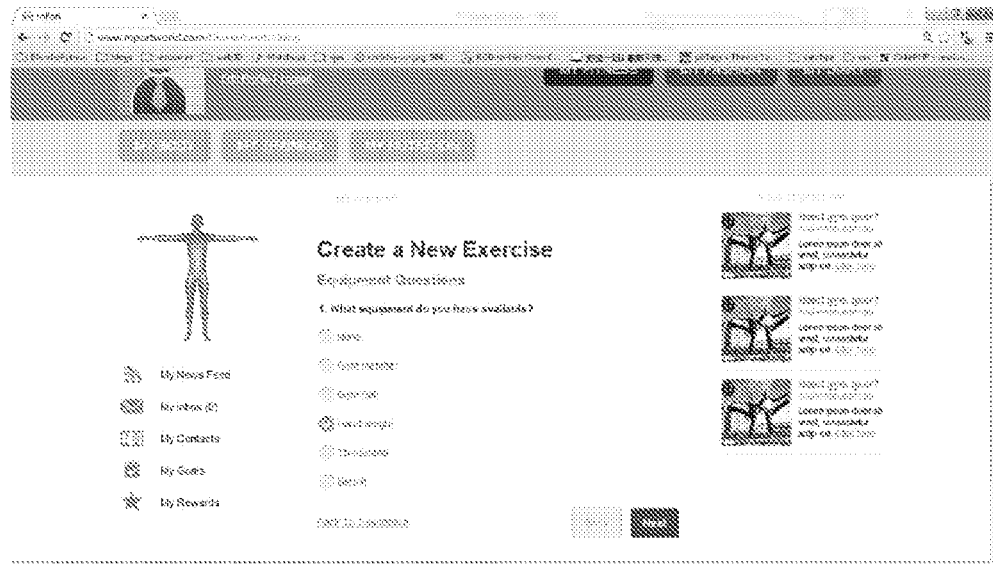
Figure 15F:
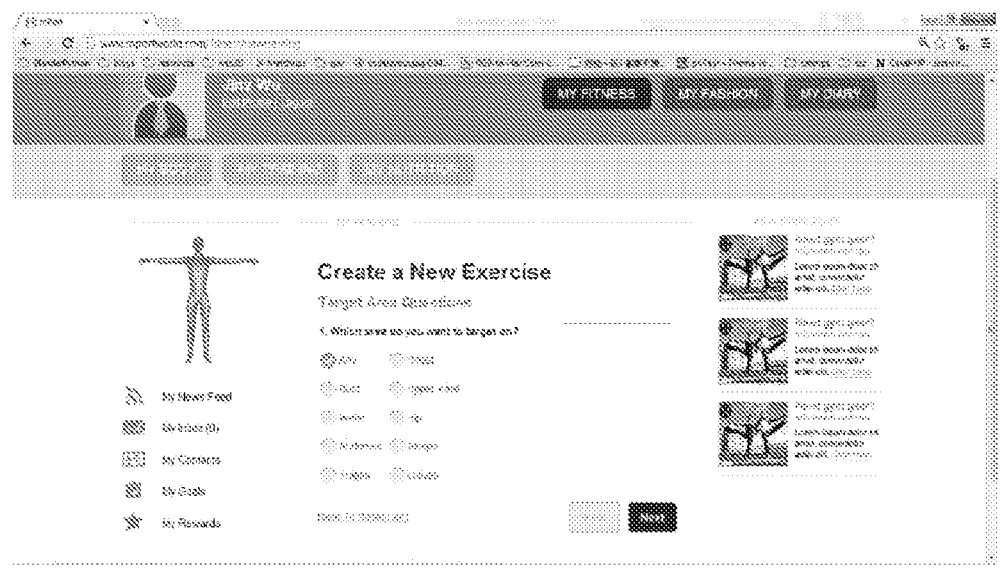
Figure 15G:
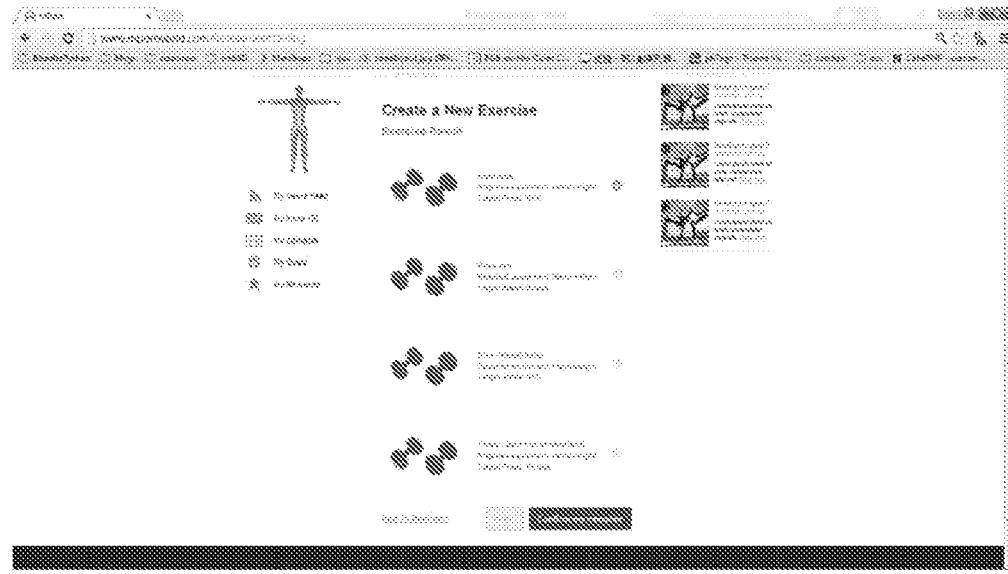
Figure 15H:
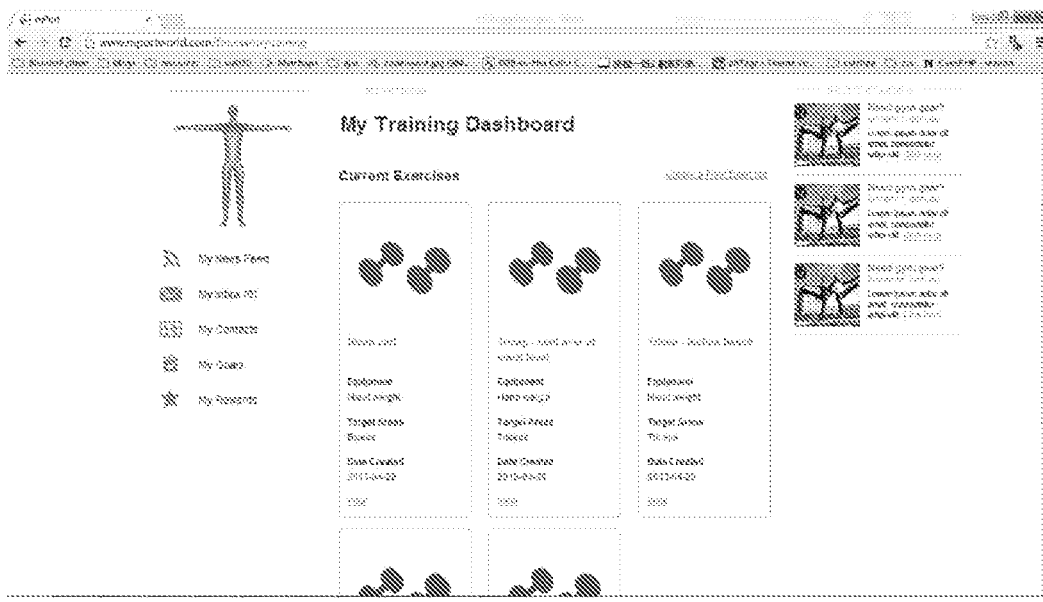
Figure 15I:
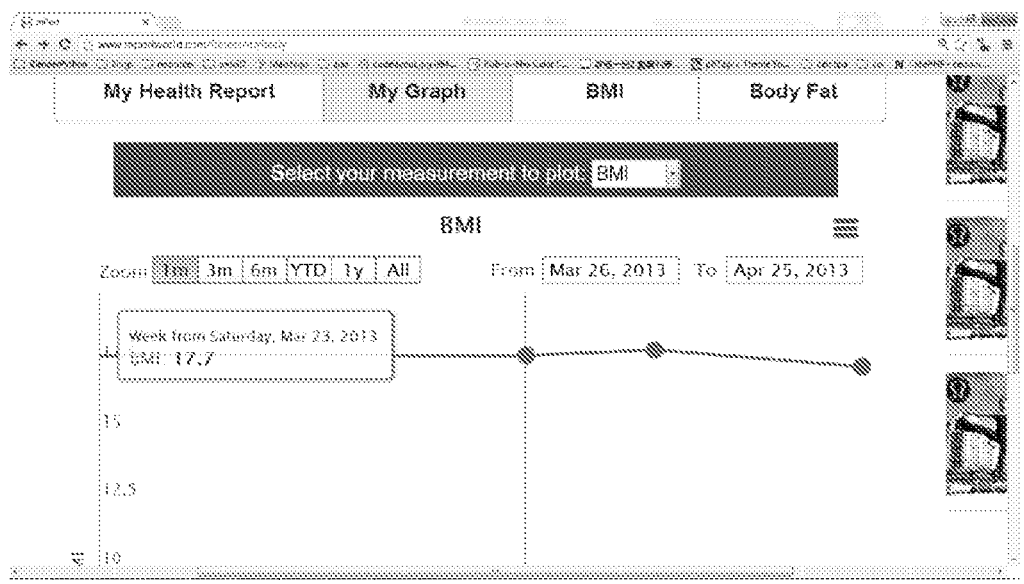

According to yet a further embodiment, the system and method described herein can provide a customised exercise plan for the user. Thus, for example, the user can be provided with a training page on a website associated with their user profile in order to develop an exercise plan. The user can use the website to create a new exercise plan, which can include answering one or more questions in relation to exercise, including and not limited to how much they currently exercise, what their goals are, where they prefer to exercise, what their preferred mode of exercise is, and the like. Once planned, the exercise routines/plan can be updated to the user's dashboard, from which the user can check their progress and confirm or archive the exercises. Example user webpages are shown in FIGS. 15A to 15I. In particular, FIG. 15I shows a graphical representation of the user's BMI being tracked over time.

Scanning Process

Figure 8:
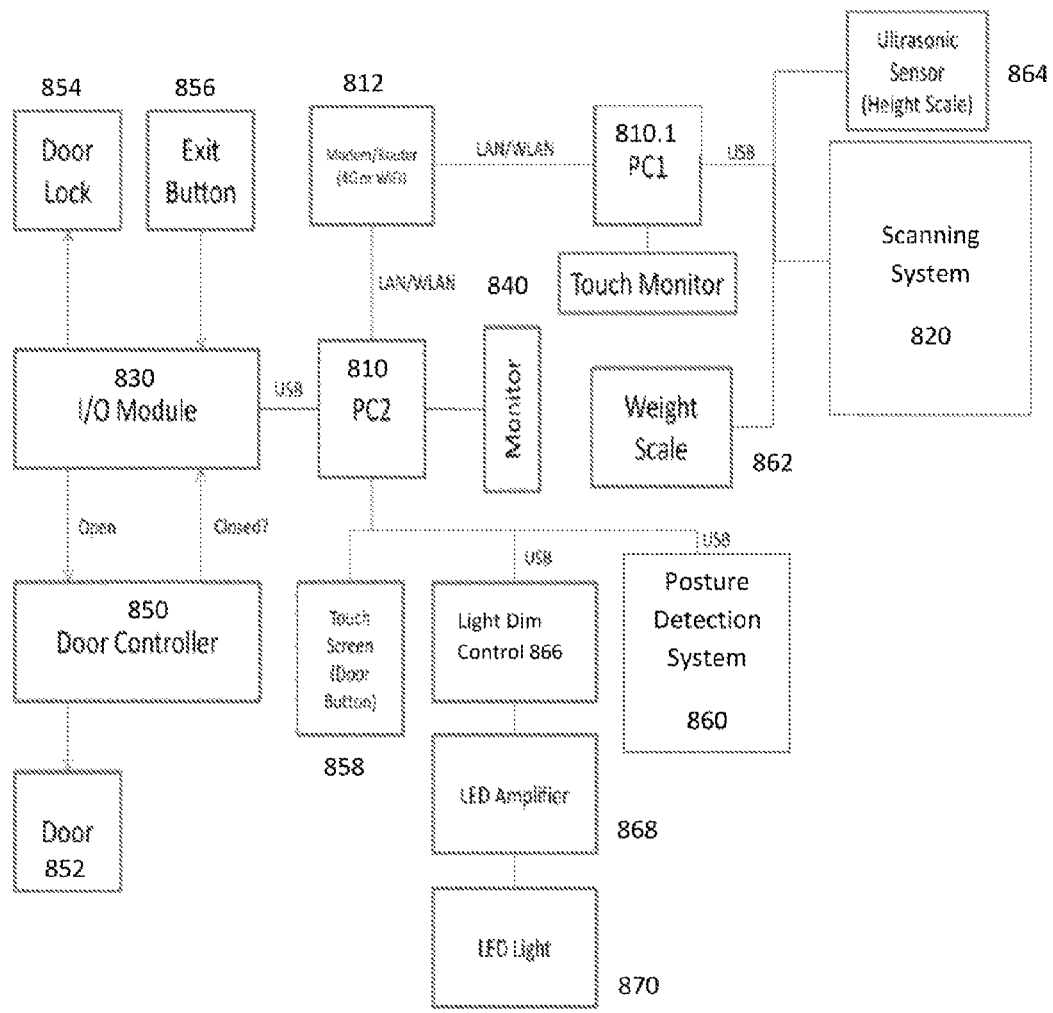
FIG. 8 is a schematic representation of another example system, which can be used to implement the methods described herein.

FIG. 8 shows a further embodiment of the system 400, where the system includes two processing systems, referred to herein as PC1 (at 810.1, otherwise referred to herein as first processing system) and PC2 (at 810, otherwise referred to herein as second processing system).

Accordingly, the two processing systems (PC1 and PC2) as shown in FIG. 8 can be responsible for certain processes within the system. In one particular example, the first processing system can send one or more requests to the second processing system for the second processing system to perform any of the process steps discussed herein. Once performed, the first processing system can receive an indication that the one or more steps have been completed. Thus, the two processing systems can share the running of the processes described herein.

Thus, for example, PC1 can be responsible for controlling/running a user interface on a touch pad which interacts with the user for signup/login and scanning (at 840), can control the scanning subsystem (at 820) as well as controlling the weight and height sensors (862 and 864). PC2 on the other hand can control a secondary user interface (also at 840), detect user posture (at 860), provide scanning progress updates via the secondary user interface at 840, as well as controlling the exit door (locking and unlocking/opening) via an I/O module 830, which can control the door lock 854 and exit button 856, the door controller 850 and thus the door at 852. PC2 can also control the touch screen door button at 858.

Furthermore, PC2 can control the lights within the booth (which, for example can be dimmable interior LED lights), which can be implemented by a light dim control at 866, and LED Amplifier at 868 and one or more connected LED lights at 870.

As also shown in FIG. 8, PC1 and PC2 can be connected via a TCP/IP protocol (transmission control protocol/internet protocol) using a LAN (local area network), via a modem or router (shown at 812). Accordingly, two processing systems PC1 and PC2 can be used to alleviate any bandwidth issues by using one processing system for receiving scanned information and generating the avatar.

In one particular example, PC1 typically leads the processes described herein. Thus, for example, system users typically interact with PC1 to drive the booth workflow shown in FIG. 2 using a touch interface inside the booth. As the user progresses from one step of the process to another PC1 requests appropriate services from PC2. Accordingly, the communication process can always be initiated by PC1. That is, PC2 does not initiate its own requests to PC1, it only executes and replies to PC1 requests. In one example, when a user activates the booth interface by touching a display such as a touch panel which is associated with PC1, sends a request to PC2 to dim the lights and lock the door. Similarly, when the user wishes to finish the process and touches PC1's "Open Door" button, a request is sent by PC1 to PC2 to unlock and open the door.

According to one particular example, when the correct posture is detected by PC2 and, PC2 in may trigger a switch in PC1 to start the measurement software.

In some embodiments PC2 provides an external display showing booth status, advertisement display, payment and/or registration interfaces, and so on.

The measurement software can include:
  using an ultrasonic height sensor to detect the height of the user In this particular example, the transducer's part of the sensor generates high frequency sound waves aimed at the user's head. Receiving part of the sensor receives the resulting echo. Time difference between sending waves and receiving the echo is then calculated and converted into distance from user's head to the sensor, which in its turn can be converted to user's height. Taking weight machine readings from USB compatible weight machine In this example, the system can user a weight scale with USB (Universal Serial Bus) physical interface. The scale can be plugged directly to PC1 USB port and provides user's weight readings to the system.
  Starting the scanning process
  Receiving the scanned information in the form of a file, typically in the form of an .obj file or .rbd file (however, it will be appreciated that the form of the file received from the scanning system can be in any form, which can then be analysed by the system herein). Using the scanned information to generate an avatar, typically, locally on PC1.
  Presenting the avatar to the user and receiving the user's confirmation via the user interface that the avatar is correct, this can include various image renditions of the human avatar. In one particular example, this can include up to 8 renditions. These may be presented in 3D. Preferably the renditions each display the avatar in different rotated views and/or perspectives.
  Once the avatar has been produced and provided to the user, the user is requested to re-dress and exit the booth.

It will further be appreciated that having a plurality of processing/computer systems (such as PC1 and PC2 can provide advantages, including but not limited to being able to balance the computing load between the two processing systems and providing easier implementation of the required functionality of the system. Thus, for example, when the CPU (Central Processing Unit) of PC1 performs an intense body scan, PC2 is able to provide a scan progress indication to the user. In yet a further embodiment, as PC1 has the responsibility for controlling the scanning system, user interaction and the representation generation and PC2 controls the door, lights and the exit button, the responsibility between the two processing systems can be shared so that one processing system (or CPU) is not entirely responsible for the entire system. Thus, this can improve the processing speed and efficiency of the system as a whole. Notably, it will be appreciated that any number of processing systems are taken to fall within the scope of the presently described system and method.

Avatar Generation

Figures 9A, 9B:
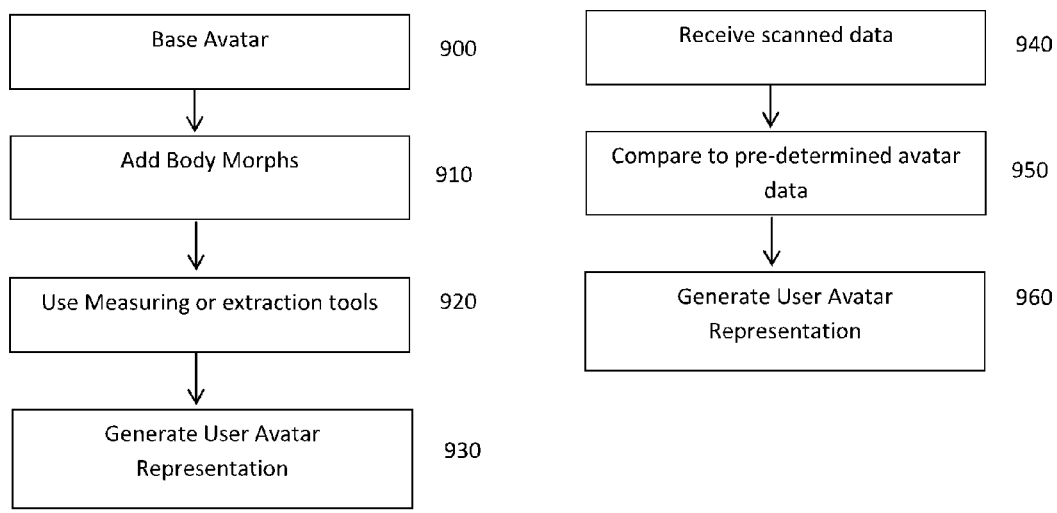
FIG. 9A and FIG. 9B are flow diagrams of further embodiments of methods described herein.

As discussed herein, a representation of the user's body can be generated by the system. In one particular example, the representation can include one or more three dimensional avatars of the user's body. FIGS. 9 to 12J show example processes and schematics for producing a three-dimensional avatar of the user's body. FIG. 9A shows, for example, a process for avatar generation. In this particular example, at step 900 a base avatar can be determined based on user's gender. In this particular example, the base avatar is typically a general avatar which can be scaled, repositioned and resized into one or more different avatars for comparison with user scanned data. At step 910 the key body landmarks of the base avatar can be repositioned to match scan data, and at step 920 resizing, scaling and shrinkwrap operation can be used to the generate the user avatar representation at step 930.

Thus, it will be appreciated that, according to one example, steps 900 and 910 can be used to generate one or more anatomically realistic user's avatars which can be stored in a data store. This process is further described in FIG. 11, below. Accordingly, once the system receives scanned data, the user's scanned data can be compared to the pre-determined avatar data which is associated with one or more generated avatars, in order to then determine the user avatar representation, thus eliminating the scaling/repositioning/resizing steps, which results in reduced time needed to present the avatar to the user. This is further shown in FIG. 9B, where at step 940 the system (that is the one or more processing systems) receive user scanned data, at step 950 the scanned data is compared to pre-determined avatar data, and at step 960 the user avatar representation is generated.

Each of the steps of FIGS. 9A and 9B are described in more detail below.

Figure 10A:
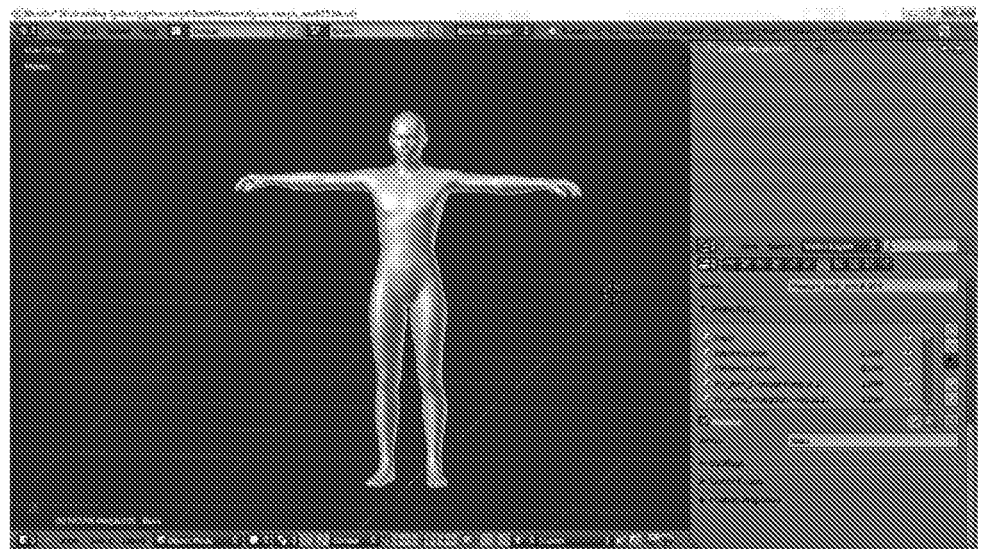
FIG. 10A to FIG. 10D are schematic representations of example screen shots showing generations of user body representations and avatars as described herein.
Figure 10B:
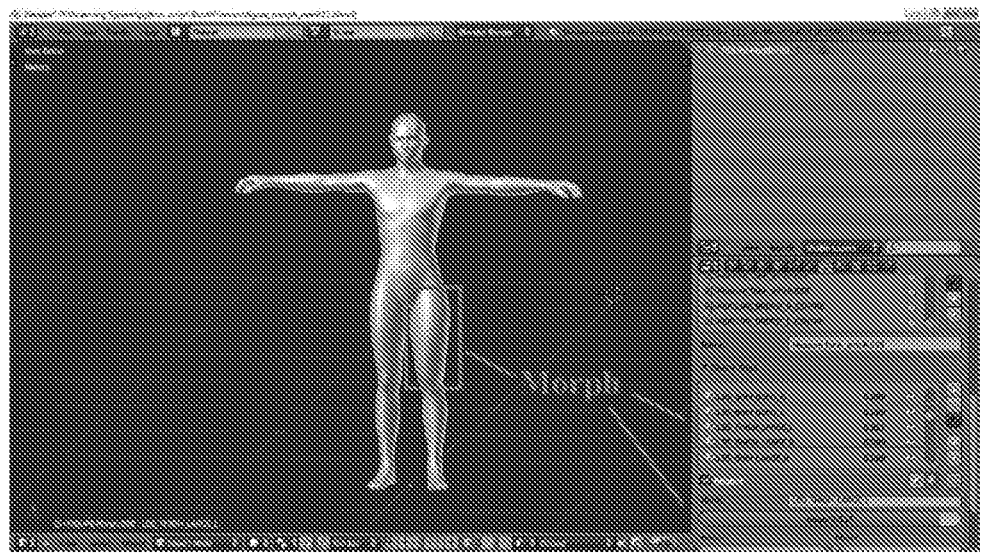

FIG. 10A shows an example of a rigged base avatar model being loaded into the present system. The system can create a plurality of body bones and control objects corresponding to the key anatomical body landmarks, an example of which is shown in FIG. 10B. In this particular example, over 100 body bones and over 50 landmarks can be created.

The data from scanner (user's measurements, user's landmarks, the point cloud) are loaded into the rigged 3D base model. The model is then scaled up or down to match the height of the scanning subject. The next step is to reposition the model's landmarks to match the actual positions of the scanning subject to reflect the user's posture. The next step is to resize all the model's parts so it would represent subjects body parts, as well as reflect the actual muscles relief. This is achieved using "shrinkwrap" operation whereas the model is wrapped and shrunk around the point cloud data received from the scanner. Finally checks are performed to ensure the model measurements are matching the measurements received from the scanner. This is done by measuring lengths and circumferences of the model at the key body points and comparing them to the actual numbers from the scanner. These key measurements include (but not limited to) chest girth, abdomen circumference, hips and thighs girth.

Figure 10C:
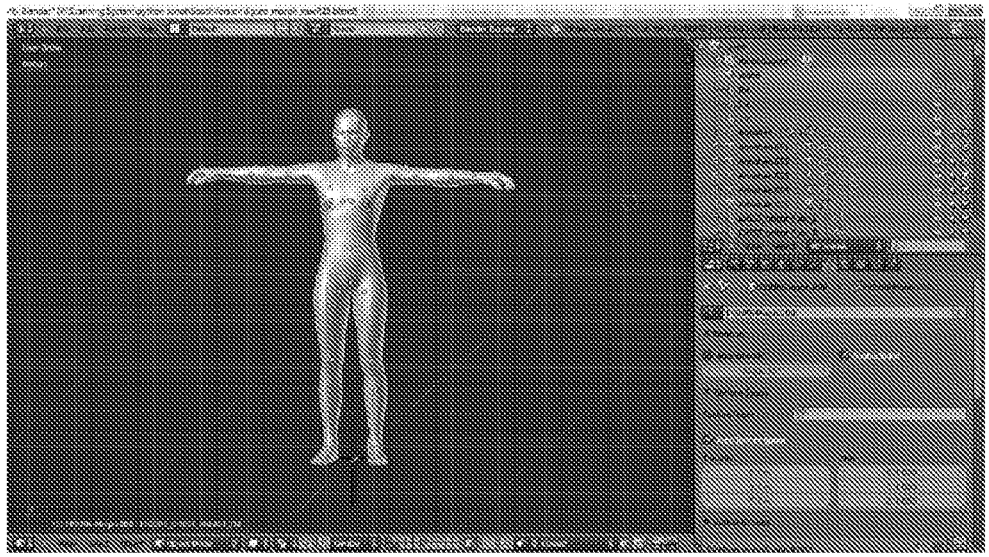
Figure 10D:
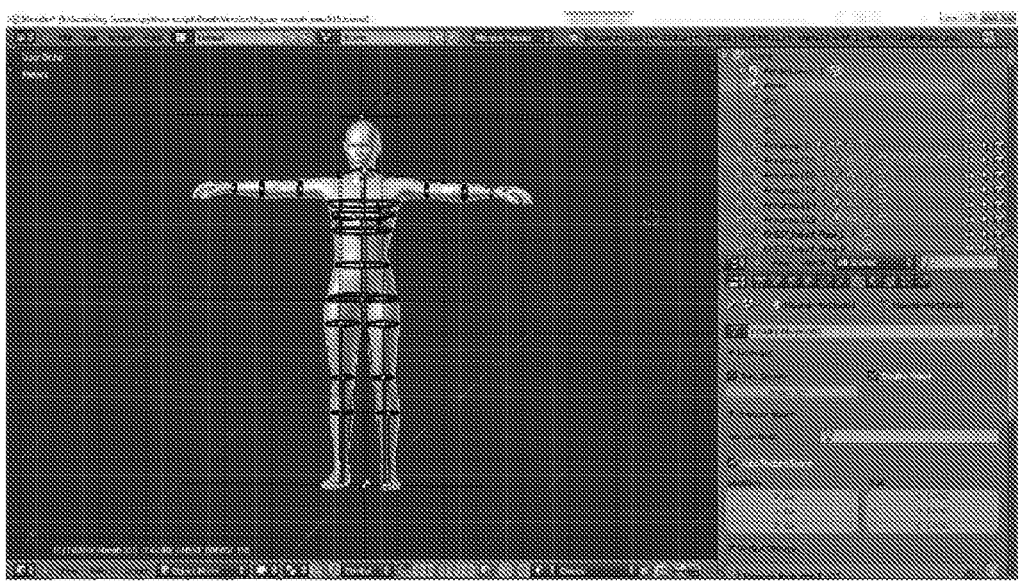

FIG. 10C shows an example of an avatar, according to a further embodiment, with hooks or key measurement points identified thereon. FIG. 10D shows an example of shrink wraps placed around the avatar, around certain hooks. FIG. 10D is typically also an example of the base avatar being saved as an altered avatar, with all of the added features.

According to one particular example, hooks are typically placed at the key locations around the body, such as, for example, at the knee, calf, and thigh. to the placement of hooks allow for the shrink wraps to be kept in place so that the shrink wraps stay around the body at all times.

Figure 11:
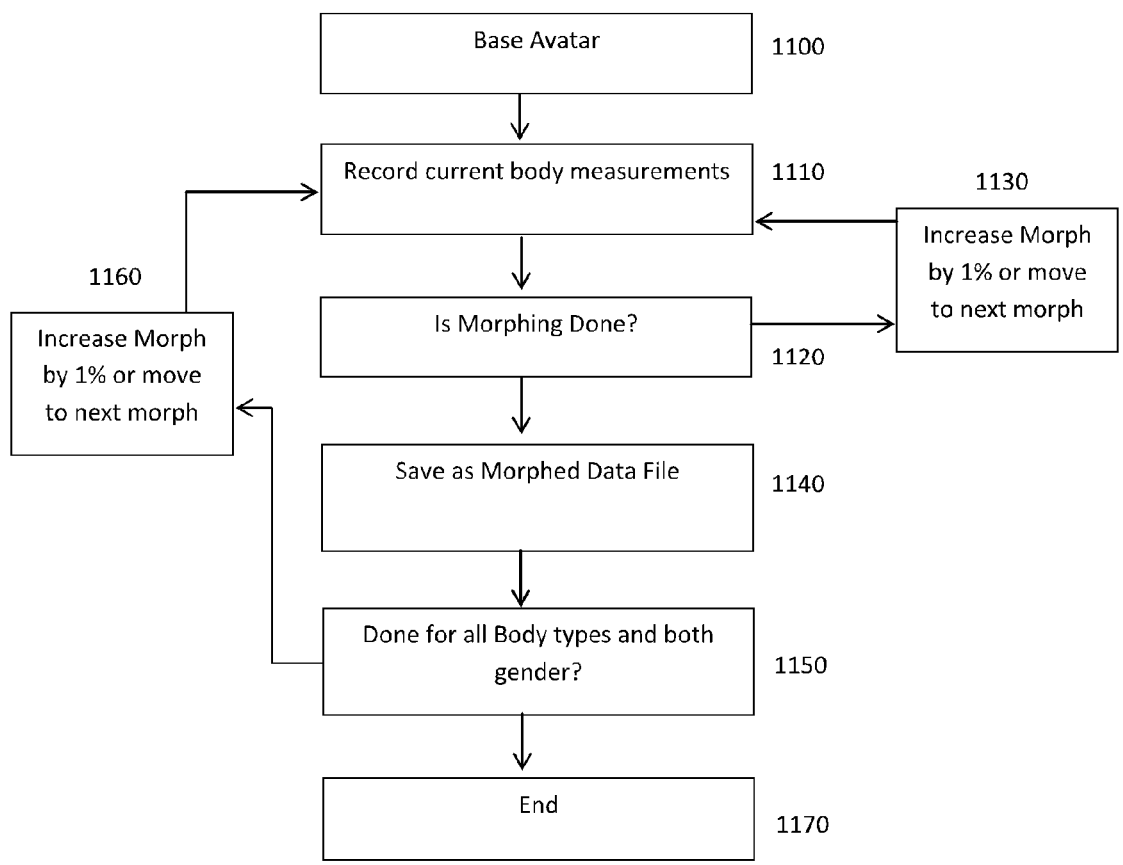
FIG. 11 is a flow diagram of a further embodiment of a method as described herein.

FIG. 11 shows an example of a process which can be applied in order to extract one or more measurements in some embodiments. At step 1100 the altered avatar, typically stored in a data store, is accessed and current body measurements are recorded at step 1110.

At step 1120 it is determined whether or not morphing is complete on the altered avatar. Thus, if morphing is not complete, the avatar is increased by 1% at step 1130. If morphing is complete, the process continues to step 1140 where the morphed avatar is now saved, typically in a data store as a data file.

At step 1150, the process determines whether morphing of the altered avatar has been completed for all body types and genders. If morphing has not been completed, then the process continues to step 1160 where the avatars to be morphed are switched to a different type. At step 1170, if morphing has occurred for all body types and genders, the process is completed.

FIG. 12 shows an example process for comparing measurements received from a scanned user's body to stored morphed avatars. In this particular example, at step 1200 the ord file with one or more morphed avatar data and the scanned data file are loaded from a data store. At step 1210 data matching is conducted between the two files. Once a match has been found, at step 1220, the scanned avatar is morphed to be matched with one or more morphed avatars. At step 1230 a scene for displaying to the user is set up and at step 1240 the image is saved against the scene. At step 1250, it is determined whether all angle views of the avatar have been covered, and if they have, then the process ends at step 1270 with a representation of the user's body having been generated. If all angles have not be considered, then the camera is rotated at step 1260 and the image is saved accordingly.

FIG. 12B shows a further embodiment where the user's scanned data (ord file), the altered avatar and the measurement data file is loaded from one or more data stores into the system. FIG. 12C shows an example of a data file, FIG. 12D shows an example of a user's scanned data and FIG. 12E shows an example of a search and match implemented on the scanned data with the measurement data in order to retrieve morphed data.

FIG. 12F shows a further embodiment of the morph data being applied to the altered avatar, in order to generate the user's avatar.

FIG. 12G shows an example of camera, lighting and texture being set up for the avatar, with FIG. 12H showing rendering of the avatar and FIG. 12 I shows an example of the camera being rotated to a different angle to complete the process. FIG. 12 J shows an example of a final image, with 360 degrees around the human avatar having been covered.

Exemplary Sizing Widget

Figure 17:
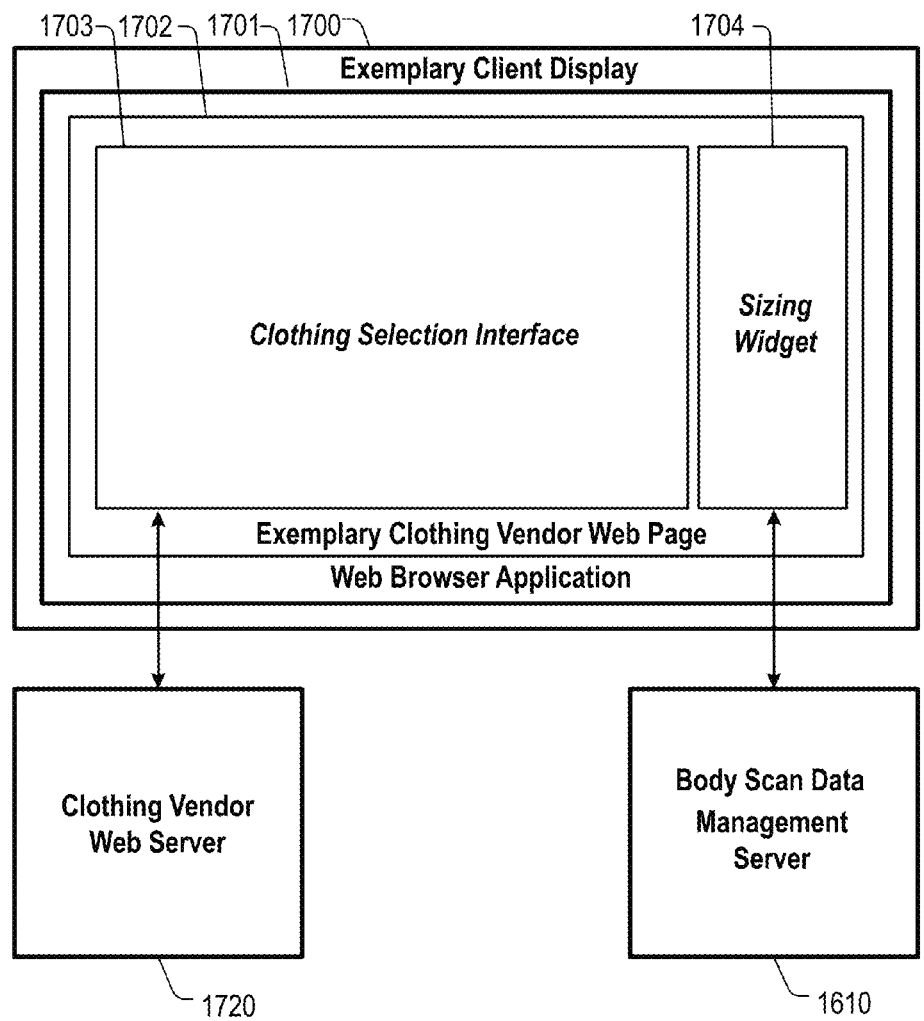
FIG. 17 illustrates an exemplary user interface arrangement according to one embodiment.

FIG. 17 illustrates an arrangement whereby a sizing widget is embedded into a third party website. More specifically, FIG. 17 represents an exemplary client display 1700 (which may be the screen of any computing device, including the likes of PCs, smartphones, tablets, and so on). A web browser application executes on a client device to which the display belongs, and that is rendered on-screen as web browser window 1701. An exemplary web page 1702 is rendered in browser window 1701, this being rendered from data obtained from a plurality of sources (for example including a primary source of web page data, and various secondary sources, including advertising servers and the like). In this example, the web page is a web page configured to allow the selection and purchase of clothing, and a clothing selection interface 1703 is rendered from data obtained from a clothing vendor web server 1720. For example, this provides images and descriptions of various garments, an ability to add garments to a "basket", and so on, as is conventional in the context of online shopping interfaces.

In addition to clothing selection interface 1703, the web page provides a sizing widget 1704, which is rendered from data downloaded from a server other than server other than server 1720, or, in other words, a server other than that which provides the clothing selection interface. This sizing widget is, in the present embodiment, rendered based on close obtained from body scan data management server 1610. However, it will be appreciated that it may also be obtained from another server which obtains body scan data from server 1610 or otherwise.

The sizing widget which integrates with a third party, or affiliate partner, website to provide information related to garment sizing for a specific user (i.e. shopper). The user performs a login via server 1610 (in some cases manually via interaction with the widget, and in some cases automatically via a locally stored token accessed by the widget), to identify themselves and have their body measurement data retrieved server 1610. These measurements are preferably calculated based on a previous 3D body scan, as described above. In some cases there is functionality to enable manual entry of measurements via the widget (optionally available to non-registered users also). The widget then provides garment sizing information (and/or recommendations), for example in the form of a recommended size, and/or fit, and/or relevant user body measurements. This in some embodiments includes a visual representation displaying how the garment would fit the identified user at predetermined locations (for example a 2D or 3D representation of the user's size/shape relative to the garment's size/shape. The sizing recommendation is calculated based on the garment detail, associated sizing rules, available sizes, and the user's body measurements. Garment sizing information is provided by the vendor (in some cases via vendor web server 1720) based on a predefined protocol (for example an electronic form that received garment size information, objectively defined sizing charts, and so on). In some cases garment sizing information is automatically deduced via extraction of data from a vendor website.

This example allows users to obtain personal sizing information and recommendations via a variety of websites, without having to share their personal sizing information with any of the websites. The users' specific personal details are isolated from the vendor, by way of the embedded widget. This is useful for both users and for an administrator of server 1610. In the context of the latter, there is specific utility in keeping valuable information they hold secure, such that the service of repeatedly providing that information may be monetised appropriately.

In some embodiments data provided by server 1610 (via the sizing widget or otherwise) is used to assist filtering available clothing options by reference to a user's size. For example, only clothing available in sizes suitable for a user are displayed (either by default, or subject to a user command).

The widget preferably is configured to remember the user's details, allowing them to continue browsing the third party, or affiliate partner's, website and receive updated garment sizing information.

Exemplary Affiliate/Tailoring Approval Widget

Following on from the preceding example, in some cases server 1610 provides an affiliate/tailoring approval widget which integrates with a third party, or affiliate partner, website and enables users to share certain body measurements with an affiliate/tailoring business. The user (i.e. shopper) can login via the widget to identify themselves and verify that they are willing to share their body measurements with the specified affiliate/tailoring business. The affiliate/tailoring business may receive a notification to alert them that the member has shared their measurement data. The widget can provide the affiliate/tailoring business with a unique member identifier, allowing them to identify the user and securely request their body measurement data. The member's body measurement data can be supplied to affiliates in real time or at a later stage. Access to the body measurements can be for a limited or indefinite time period. This allows for the tailoring of custom clothing based on a suer's specific sizing needs.

Affiliate/Tailoring Approval Backend Portal

In some embodiments server 1610 provides a secure online portal/website which allows affiliate partners (e.g. tailoring businesses, clothing vendors, and the like) to login and access certain member body measurements belonging to members. Affiliates can only access body measurement data belonging to members who have pre-approved their data to be shared with the specific affiliate. Affiliates who access the portal must be approved by mPort before they can access any member data. Each affiliate request to view member measurement data is recorded. Affiliates can view the member measurements via a web browser, and request them to be emailed to their account or downloaded in another format.

Exemplary Measurement-Based Promotional Methods

In some embodiments, a proximity-based matching algorithm is applied thereby to identify vendors and/or specific garments proximal a user (based on mobile device location, assessed using GPS or other means) based upon their body scan data and/or other parameters. This is preferably used thereby to assist a user in identifying garments suitable for their size in nearby locations, in some cases limited to garments for which special prices or the like are being offered. This, in some embodiments, is based upon matching of fit parameters provided by vendors and sizing data determined for a given user.

In some embodiments this algorithm is applied via a mobile app, for example thereby to provide a "Find clothes nearby" functionality. Recommendations may be filtered by brand, colour, price, discount, and/or other parameters.
—Recommendations may will take into account factors including but not limited to Previous purchases;
Purchases made by people of similar measurements; and
Purchasing preferences indicated by the user.

In further embodiments proximity-based matching is implemented in broader context, for example in relation to health/fitness applications as opposed to clothing sizes.

Exemplary Alterations Management Process

In some embodiments, body scan data (for example user sizing data) is used thereby to assist in providing alternations services to users. As with embodiments described above, this may include the user of a widget-based approach whereby embedded objects provided in vendor web pages. An exemplary approach is illustrated in FIG. 19.

Figure 19:
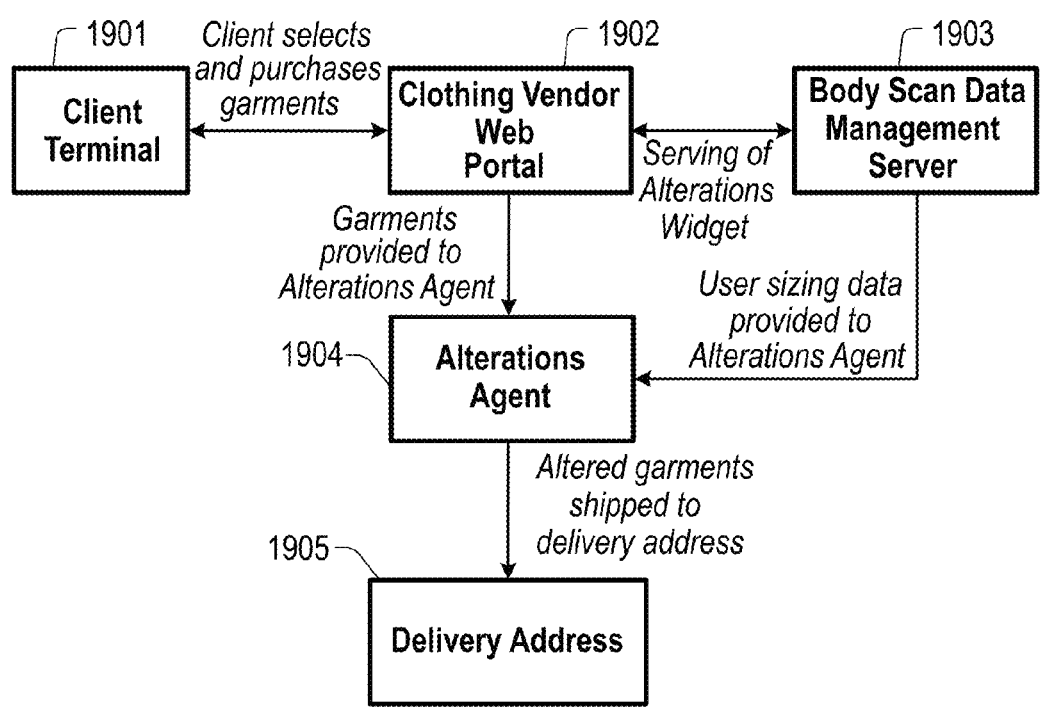
FIG. 19 illustrates an alterations arrangement according to one embodiment.

In the example of FIG. 19, a user operates a client terminal 1901 thereby to interact with a clothing vendor web portal 1902 (for example a website from which clothing garments are able to be purchased). Body scan management data server 1903 (or in some embodiments a server associated with a body scan data management service) provides code indicative of an alterations widget, which is rendered in a web page viewed by the client (the code in some embodiments is downloaded directly to the client terminal, as opposed to being downloaded via portal 1902). This provides an option for the client to "purchase altered clothing" or the like. In some cases this option is able to be applied to individual selected garments, optionally with further user-specified customisation options.

In the case that the user selects an option to purchase altered clothing for one or more garments, those garments (and optionally other garments in a common order) are provided to an alternations agent 1904 for altering prior to delivery to a delivery address 1905 designated by the user. Server 1903 provides user sizing data to agent 1904 (directly or indirectly) thereby to facilitate the alterations. For example, in one embodiment server 1903 provides work order data to agent 1904, this specifying an order placed via portal 1902, garments for which alteration is required (and any user-defined customisation options), and user sizing information derived from body scan data. The ultimate delivery address 1905 may also be provided.

In some embodiments, alterations functionality is integrated such that the overall user checkout procedure is substantially unaffected. The consumer need only select a "purchase altered clothing", which automatically adds a service charge to a billing total amount (unless the service is provide complimentarily). This consumer continues with the purchase as per usual, and the shipping of garments to agent 1904 (or other delivery), and charging of the vendor for alterations, are handled as back-office operations (preferably automated) without concern to the user.

Exemplary Client Server Framework

Figure 18:
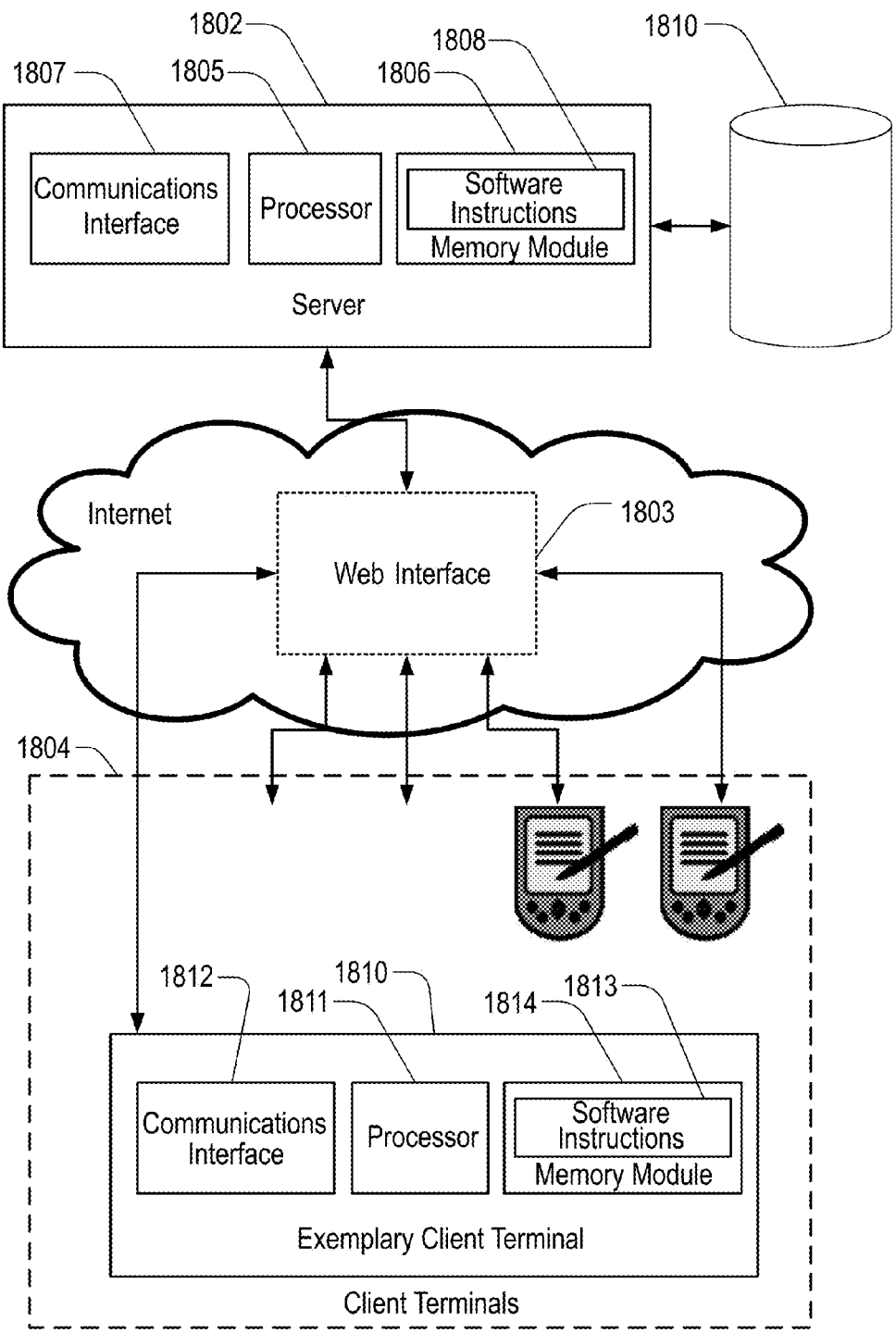
FIG. 18 illustrates an exemplary client-server framework leveraged by various embodiments.

In some embodiments, methods and functionalities considered herein leverage a client-server framework, for example as illustrated in FIG. 18. In overview, a web server 1802 provides a web interface 1803. This web interface is accessed by the parties by way of client terminals 1804. In overview, users access interface 1803 over the Internet by way of client terminals 1804, which in various embodiments include the likes of personal computers, PDAs, cellular telephones, gaming consoles, and other Internet enabled devices.

Server 1803 includes a processor 1805 coupled to a memory module 1806 and a communications interface 1807, such as an Internet connection, modem, Ethernet port, wireless network card, serial port, or the like. In other embodiments distributed resources are used. For example, in one embodiment server 1802 includes a plurality of distributed servers having respective storage, processing and communications resources. Memory module 1806 includes software instructions 1808, which are executable on processor 1805.

Server 1802 is coupled to a database 1810. In further embodiments the database leverages memory module 1806.

In some embodiments web interface 1803 includes a website. The term "website" should be read broadly to cover substantially any source of information accessible over the Internet or another communications network (such as WAN, LAN or WLAN) via a browser application running on a client terminal. In some embodiments, a website is a source of information made available by a server and accessible over the Internet by a web-browser application running on a client terminal. The web-browser application downloads code, such as HTML code, from the server. This code is executable through the web-browser on the client terminal for providing a graphical and often interactive representation of the website on the client terminal. By way of the web-browser application, a user of the client terminal is able to navigate between and throughout various web pages provided by the website, and access various functionalities that are provided.

Although some embodiments make use of a website/browser-based implementation, in other embodiments proprietary software methods are implemented as an alternative. For example, in such embodiments client terminals 1804 maintain software instructions for a computer program product that essentially provides access to a portal via which framework 100 is accessed (for instance via an iPhone app or the like).

In general terms, each terminal 1804 includes a processor 1811 coupled to a memory module 1813 and a communications interface 1812, such as an internet connection, modem, Ethernet port, serial port, or the like. Memory module 1813 includes software instructions 1814, which are executable on processor 1811. These software instructions allow terminal 1804 to execute a software application, such as a proprietary application or web browser application and thereby render on-screen a user interface and allow communication with server 1802. This user interface allows for the creation, viewing and administration of profiles, access to the internal communications interface, and various other functionalities.

CONCLUSIONS AND INTERPRETATION

It will be appreciated that the disclosure above provides various significant devices, frameworks and methodologies for enabling user-driven determination of body size and shape information and utilisation of such information across a networked environment.

Unless specifically stated otherwise, as apparent from the following discussions, it is appreciated that throughout the specification discussions utilizing terms such as "processing," "computing," "calculating," "determining", analyzing" or the like, refer to the action and/or processes of a computer or computing system, or similar electronic computing device, that manipulate and/or transform data represented as physical, such as electronic, quantities into other data similarly represented as physical quantities.

In a similar manner, the term "processor" may refer to any device or portion of a device that processes electronic data, e.g., from registers and/or memory to transform that electronic data into other electronic data that, e.g., may be stored in registers and/or memory. A "computer" or a "computing machine" or a "computing platform" may include one or more processors.

The methodologies described herein are, in one embodiment, performable by one or more processors that accept computer-readable (also called machine-readable) code containing a set of instructions that when executed by one or more of the processors carry out at least one of the methods described herein. Any processor capable of executing a set of instructions (sequential or otherwise) that specify actions to be taken are included. Thus, one example is a typical processing system that includes one or more processors. Each processor may include one or more of a CPU, a graphics processing unit, and a programmable DSP unit. The processing system further may include a memory subsystem including main RAM and/or a static RAM, and/or ROM. A bus subsystem may be included for communicating between the components. The processing system further may be a distributed processing system with processors coupled by a network. If the processing system requires a display, such a display may be included, e.g., a liquid crystal display (LCD) or a cathode ray tube (CRT) display. If manual data entry is required, the processing system also includes an input device such as one or more of an alphanumeric input unit such as a keyboard, a pointing control device such as a mouse, and so forth. The term memory unit as used herein, if clear from the context and unless explicitly stated otherwise, also encompasses a storage system such as a disk drive unit. The processing system in some configurations may include a sound output device, and a network interface device. The memory subsystem thus includes a computer-readable carrier medium that carries computer-readable code (e.g., software) including a set of instructions to cause performing, when executed by one or more processors, one of more of the methods described herein. Note that when the method includes several elements, e.g., several steps, no ordering of such elements is implied, unless specifically stated. The software may reside in the hard disk, or may also reside, completely or at least partially, within the RAM and/or within the processor during execution thereof by the computer system. Thus, the memory and the processor also constitute computer-readable carrier medium carrying computer-readable code.

Furthermore, a computer-readable carrier medium may form, or be included in a computer program product.

In alternative embodiments, the one or more processors operate as a standalone device or may be connected, e.g., networked to other processor(s), in a networked deployment, the one or more processors may operate in the capacity of a server or a user machine in server-user network environment, or as a peer machine in a peer-to-peer or distributed network environment. The one or more processors may form a personal computer (PC), a tablet PC, a set-top box (STB), a Personal Digital Assistant (PDA), a cellular telephone, a web appliance, a network router, switch or bridge, or any machine capable of executing a set of instructions (sequential or otherwise) that specify actions to be taken by that machine.

Note that while diagrams only show a single processor and a single memory that carries the computer-readable code, those in the art will understand that many of the components described above are included, but not explicitly shown or described in order not to obscure the inventive aspect. For example, while only a single machine is illustrated, the term "machine" shall also be taken to include any collection of machines that individually or jointly execute a set (or multiple sets) of instructions to perform any one or more of the methodologies discussed herein.

Thus, one embodiment of each of the methods described herein is in the form of a computer-readable carrier medium carrying a set of instructions, e.g., a computer program that is for execution on one or more processors, e.g., one or more processors that are part of web server arrangement. Thus, as will be appreciated by those skilled in the art, embodiments of the present invention may be embodied as a method, an apparatus such as a special purpose apparatus, an apparatus such as a data processing system, or a computer-readable carrier medium, e.g., a computer program product. The computer-readable carrier medium carries computer readable code including a set of instructions that when executed on one or more processors cause the processor or processors to implement a method. Accordingly, aspects of the present invention may take the form of a method, an entirely hardware embodiment, an entirely software embodiment or an embodiment combining software and hardware aspects. Furthermore, the present invention may take the form of carrier medium (e.g., a computer program product on a computer-readable storage medium) carrying computer-readable program code embodied in the medium.

The software may further be transmitted or received over a network via a network interface device. While the carrier medium is shown in an exemplary embodiment to be a single medium, the term "carrier medium" should be taken to include a single medium or multiple media (e.g., a centralized or distributed database, and/or associated caches and servers) that store the one or more sets of instructions. The term "carrier medium" shall also be taken to include any medium that is capable of storing, encoding or carrying a set of instructions for execution by one or more of the processors and that cause the one or more processors to perform any one or more of the methodologies of the present invention. A carrier medium may take many forms, including but not limited to, non-volatile media, volatile media, and transmission media. Non-volatile media includes, for example, optical, magnetic disks, and magneto-optical disks. Volatile media includes dynamic memory, such as main memory. Transmission media includes coaxial cables, copper wire and fiber optics, including the wires that comprise a bus subsystem. Transmission media also may also take the form of acoustic or light waves, such as those generated during radio wave and infrared data communications. For example, the term "carrier medium" shall accordingly be taken to included, but not be limited to, solid-state memories, a computer product embodied in optical and magnetic media; a medium bearing a propagated signal detectable by at least one processor of one or more processors and representing a set of instructions that, when executed, implement a method; and a transmission medium in a network bearing a propagated signal detectable by at least one processor of the one or more processors and representing the set of instructions.

It will be understood that the steps of methods discussed are performed in one embodiment by an appropriate processor (or processors) of a processing (i.e., computer) system executing instructions (computer-readable code) stored in storage. It will also be understood that the invention is not limited to any particular implementation or programming technique and that the invention may be implemented using any appropriate techniques for implementing the functionality described herein. The invention is not limited to any particular programming language or operating system.

It should be appreciated that in the above description of exemplary embodiments of the invention, various features of the invention are sometimes grouped together in a single embodiment, FIG., or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those skilled in the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

In the description provided herein, numerous specific details are set forth. However, it is understood that embodiments of the invention may be practiced without these specific details. In other instances, well-known methods, structures and techniques have not been shown in detail in order not to obscure an understanding of this description.

Similarly, it is to be noticed that the term coupled, when used in the claims, should not be interpreted as being limited to direct connections only. The terms "coupled" and "connected," along with their derivatives, may be used. It should be understood that these terms are not intended as synonyms for each other. Thus, the scope of the expression a device A coupled to a device B should not be limited to devices or systems wherein an output of device A is directly connected to an input of device B. It means that there exists a path between an output of A and an input of B which may be a path including other devices or means. "Coupled" may mean that two or more elements are either in direct physical or electrical contact, or that two or more elements are not in direct contact with each other but yet still co-operate or interact with each other.

Thus, while there has been described what are believed to be the preferred embodiments of the invention, those skilled in the art will recognize that other and further modifications may be made thereto without departing from the spirit of the invention, and it is intended to claim all such changes and modifications as falling within the scope of the invention. For example, any formulas given above are merely representative of procedures that may be used. Functionality may be added or deleted from the block diagrams and operations may be interchanged among functional blocks. Steps may be added or deleted to methods described within the scope of the present invention.

The invention claimed is:

1. A scanning booth system configured to enable determination of physical body shape data for a user, the system including:
  a processing system, wherein the processing system is configured to receive measurement input data from a plurality of connected sensor devices;
  a structural assembly defining a booth interior, wherein the booth interior is securely concealed from exterior view, and wherein the booth interior is sized thereby to enable undressing and dressing of a user contained therein;
  a standing area including floor markings that define a predetermined foot position, wherein the floor markings are provided on a weight scale, wherein the weight scale defines one of the plurality of connected sensor devices;

a height sensor device positioned vertically above the standing area, wherein the height sensor defines one of the plurality of connected sensor devices, wherein the height sensor device is configured to measure height of a user standing in the predetermined foot position;

a user interface device configured to receive identification information from a user, wherein the user interface device includes a touchscreen terminal positioned to be in front of a user standing in the predetermined foot position;

one or more stimuli devices coupled to a control device, wherein the control device is configured to implement a logical instructions process flow thereby to provide, via the one or more stimuli devices, instructions to a user contained within the booth interior, wherein the instructions include instructions for the user to adopt a predefined stance, position and posture, wherein the one or more stimuli devices include a display unit of the touchscreen terminal;

a plurality of scanning devices configured to derive measurements representative of size of a body contained within the booth interior, wherein the plurality of scanning devices include a plurality of infrared scanners configured to collectively capture a 360 degrees scan of a user standing in the predetermined foot position, wherein the plurality of scanning devices define a subset of the plurality of connected sensor devices;

a communications module configured to enable communication between the scanning booth and a central server, wherein the communications module is configured to transmit, to the central server, user health data including body scan data derived from the plurality of connected sensor devices, including output of the one or more scanning devices; and a display unit configured to provide to the user a visual representation of a three dimensional avatar defined based upon the output of the one or more scanning devices;

wherein:

the identification information received by the user is processed by the central server thereby to identify a user profile for an identified user, wherein the user profile is associated with historical user health data for the identified user including body scan data derived from the scanning booth system or another similar networked scanning booth system; and the central server is configured to compare the user health data including body scan data with the historical user health data including body scan data, thereby to generate report data representative of tracking against one or more goals, wherein the goals are defined relative to desired changes in future user health data including body scan data.

2. A system according to claim 1 wherein the structural assembly includes handles which are configured to be manually grasped, thereby to provide instructions as to body pose.

3. A system according to claim 1 wherein the structural assembly includes a floor including a primary-textured region and a secondary-textured region, such that a user is able to determine when they are standing in the secondary-textured region, thereby to provide instructions as to stance.

4. A system according claim 1 wherein the user interface device is configured to enable each of the following: input of user identification information representative of a user account previously created at the scanning booth; input of user identification information representative of a user account previously created at a further scanning booth; input of user identification information representative of a user account previously created via a user client terminal that interacts with a web server; and generation of a new user account.

5. A system according to claim 1 wherein the three-dimensional avatar is generated by morphing a generic base avatar based on comparison with measurements devices from operation of the one or more scanning devices, thereby to define an avatar having size parameters representative of the user.

6. A system according to claim 1 wherein the three-dimensional avatar is generated by applying a shrink-wrapping and smoothing algorithm to point cloud data obtained from infrared scan data thereby to provide an indicative representation of the user based on the user's size parameters.

7. A system according to claim 5 wherein the three dimensional avatar is not a direct graphical representation of the user.

8. A system according to claim 1 wherein the three dimensional avatar is uploaded to the server, and made available for embedding into user interface objects in third party websites.

9. A system according to claim 8 wherein the three dimensional avatar is configured to provide a graphical indication size of a specified garment relative to size of the user.

10. A data management system including:

an input interface configured to receive, from a plurality of scanning booth systems, body scan data respectively defined for a plurality of users;

a data repository configured to maintain user record data, wherein the user record data is configured to include, for each of a plurality of users, user registration data and user body scan data; and one or more integration modules, wherein the integration modules are configured to provide one or more aspects of the body scan data to one or more third party platforms;

wherein each of the plurality of scanning booth systems include a scanning booth system configured to enable determination of physical body shape data for a user, the system including:

a processing system, wherein the processing system is configured to receive measurement input data from a plurality of connected sensor devices;

a structural assembly defining a booth interior, wherein the booth interior is securely concealed from exterior view, and wherein the booth interior is sized thereby to enable undressing and dressing of a user contained therein;

a standing area including floor markings that define a predetermined foot position, wherein the floor markings are provided on a weight scale, wherein the weight scale, wherein the weight scale defines one of the plurality of connected sensor devices;

a height sensor device positioned vertically above the standing area, wherein the height sensor defines one of the plurality of connected sensor devices, wherein the height sensor device is configured to measure height of a user standing in the predetermined foot position;

a user interface device configured to receive identification information from a user, wherein the user interface device includes a touchscreen terminal positioned to be in front of a user standing in the predetermined foot position;

one or more stimuli devices coupled to a control device, wherein the control device is configured to implement a logical instructions process flow thereby to provide, via the one or more stimuli devices, instructions to a user contained within the booth interior, wherein the instructions include instructions for the user to adopt a predefined stance, position and posture, wherein the one or more stimuli devices include a display unit of the touchscreen terminal;

a plurality of scanning devices configured to derive measurements representative of size of a body contained within the booth interior, wherein the plurality of scanning devices include a plurality of infrared scanners configured to collectively capture a 360 degrees scan of a user standing in the predetermined foot position, wherein the plurality of scanning devices define a subset of the plurality of connected sensor devices;

a communications module configured to enable communication between the scanning booth and a central server, wherein the communications module is configured to transmit, to the central server, user health data including body scan data derived from the plurality of connected sensor devices, including output of the one or more scanning devices; and a display unit configured to provide to the user a visual representation of a three dimensional avatar defined based upon the output of the one or more scanning devices;

wherein:

the identification information received by the user is processed by the central server thereby to identify a particular set of the user record data for an identified user, wherein the user profile is associated with historical user health data including body scan data for that identified user derived from the scanning booth system or another similar networked scanning booth system; and the central server is configured to compare the user health data including body scan data with the historical user health data including body scan data, thereby to generate report data representative of tracking against one or more goals, wherein the goals are defined relative to desired changes in future user health data including body scan data.

11. A system according to claim 10 wherein the one or more third party platforms include third party web pages.

12. A system according to claim 11 wherein each third party web page includes embedded code referencing a widget object served by the one or more integration modules.

13. A system according to claim 10 wherein the one or more third party platforms include third party software applications which interact with the one or more integration modules via an API.

14. A system according to claim 11 wherein the integration modules include an integration module configured to assist in identifying garments, displayed on a third party website, which are suitable based on a given user's sizing data as derived from body scan data.

15. A system according to claim 10 wherein the one or more integration modules provide functionalities including: size-based filtering of garments advertised for sale at a third party website.

16. A system according to claim 10 wherein the one or more integration modules provide functionalities including: provision of a clothing alteration service.

* * * * *